US012662441B2

(12) United States Patent
Subramaniam et al.

(10) Patent No.: US 12,662,441 B2
(45) Date of Patent: *Jun. 23, 2026

(54) ACTIVATION OF ALKYL SUBSTRATES IN CONDENSED PHASE WITH OZONE

(71) Applicant: University of Kansas, Lawrence, KS (US)

(72) Inventors: Bala Subramaniam, Lawrence, KS (US); Hongda Zhu, Lawrence, KS (US); Timothy A. Jackson, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 587 days.

This patent is subject to a terminal disclaimer.

(21) Appl. No.: 18/194,814

(22) Filed: Apr. 3, 2023

(65) Prior Publication Data

US 2023/0339830 A1 Oct. 26, 2023

Related U.S. Application Data

(60) Provisional application No. 63/327,531, filed on Apr. 5, 2022.

(51) Int. Cl.
*C07C 29/50* (2006.01)
*C07C 29/94* (2006.01)

(52) U.S. Cl.
CPC .............. *C07C 29/50* (2013.01); *C07C 29/94* (2013.01)

(58) Field of Classification Search
USPC ........................................................ 568/954
See application file for complete search history.

(56) References Cited

U.S. PATENT DOCUMENTS

| | | | |
|---|---|---|---|
| 3,957,876 | A | 5/1976 | Rapoport et al. |
| 4,038,322 | A | 7/1977 | De Radzitzky D'Ostrowick et al. |
| 6,350,919 | B1 | 2/2002 | Hagen et al. |
| 8,801,939 | B2 | 8/2014 | Subramaniam et al. |
| 2003/0100805 | A1 | 5/2003 | Subramaniam et al. |
| 2008/0087348 | A1 | 4/2008 | Gillis et al. |
| 2012/0037490 | A1 | 2/2012 | Kapila et al. |
| 2012/0053354 | A1 | 3/2012 | Yoshida |
| 2013/0240781 | A1 | 9/2013 | Subramaniam et al. |
| 2014/0065047 | A1 | 3/2014 | Hui et al. |
| 2014/0124381 | A1 | 5/2014 | Fan |
| 2019/0177254 | A1 | 6/2019 | Subramaniam et al. |
| 2024/0124379 | A1 | 4/2024 | Subramaniam et al. |

FOREIGN PATENT DOCUMENTS

| | | | |
|---|---|---|---|
| CN | 102757302 | A | 10/2012 |
| CN | 107162167 | A | 9/2017 |
| DE | 19811517 | A1 | 9/1999 |
| WO | WO 2020/173885 | A1 | 9/2020 |
| WO | WO 2022/192866 | A1 | 9/2022 |

OTHER PUBLICATIONS

Bozovic et al., "Conversion of methane to methanol: nickel, palladium, and platinum (d9) cations as catalysts for the oxidation of methane by ozone at room temperature," Chemistry, Oct. 11, 2010, vol. 16, No. 38, pp. 11605-11610.
Lundin et al., "Liquid CO2 as a Safe and Benign Solvent for the Ozonolysis of Fatty Acid Methyl Esters," ACS Sustainable Chem. Eng., 2015, vol. 3, No. 12, pp. 3307-3314.
The International Search Report & Written Opinion dated Oct. 24, 2017 issued in International Patent Application No. PCT/US17/46258, pp. 1-8.
Zhu et al., "Highly Selective Isobutane Hydroxylation by Ozone in a Pressure-Tuned Biphasic Gas-Liquid Process," *ACS Sustainable Chem. Eng.* 2021, 9, 16, 5506-5512.
Zhu, Hongda, Timothy A. Jackson, and Bala Subramaniam, "Facile Ozonation of Light Alkanes to Oxygenates with High Atom Economy in Tunable Condensed Phase at Ambient Temperature," *JACS Au* (2023), 3, 498-507.

*Primary Examiner* — Ana Z Muresan
(74) *Attorney, Agent, or Firm* — Bell & Manning, LLC

(57) ABSTRACT

A process for oxidizing an alkyl substrate may comprise combining an alkyl substrate (e.g., propane, n-butane) and ozone in a liquid phase medium comprising a branched alkane activator (e.g., isobutane) and a protic additive (e.g., water) under conditions sufficient to oxidize the alkyl substrate to products. The alkyl substrate may be selected from linear and cyclic alkanes.

20 Claims, 13 Drawing Sheets

Left bar key (same vertical
order as in graph)

CO₂
Formic acid (FA)
Acetic acid (HOAc)
Propionic acid (PA)
Acetone (Ace)
Butyric acid (BA)
2-Butanone (MEK)
2-Butanol (SBA)
*tert*-Butanol (TBA)

Right bar key

O₃ utilization 0.3 mol $C_4H_{10}$, 25 °C, 3.1±0.1 mmol O₃,
5% O₃ in 0.34 MPa gases in reactor,
average residence time 6 min.

i-C₄ initially 100 μL H₂O

77%

CO₂ 6.0%

Ace 6.4%

TBA 85.7%

$X_{i-C_4}$ = 1.3%
±0.03% i/n=2.0

75%

CO₂ 7.2%

Ace 6.0%
MEK 11.5%
SBA 5.0%

TBA 65.5%

$X_{i-C_4}$ = 0.86%
$X_{n-C_4}$ = 0.34%
±0.04% i/n=1.2

83%

CO₂ 8.8%

HOAc 2.0%
Ace 8.8%

MEK 15.0%

SBA 7.1%

TBA 55.4%

$X_{i-C_4}$ = 0.77%
$X_{n-C_4}$ = 0.43%
±0.05% i/n=0.5

97%

CO₂ 5.4%

FA 2.0%
HOAc 2.4%
Ace 7.3%

MEK 25.9%

SBA 9.3%

TBA 41.0%

$X_{i-C_4}$ = 0.76%
$X_{n-C_4}$ = 0.64%
±0.05% n-C₄

98%

CO₂ 2.3%
FA 4.5%
HOAc 10.9%
PA 5.0%
BA 3.2%

MEK 52.8%

$X_{n-C_4}$ = 0.9%
±0.02%

SBA 19.0%

Butane feed

Product selectivity or O₃ utilization

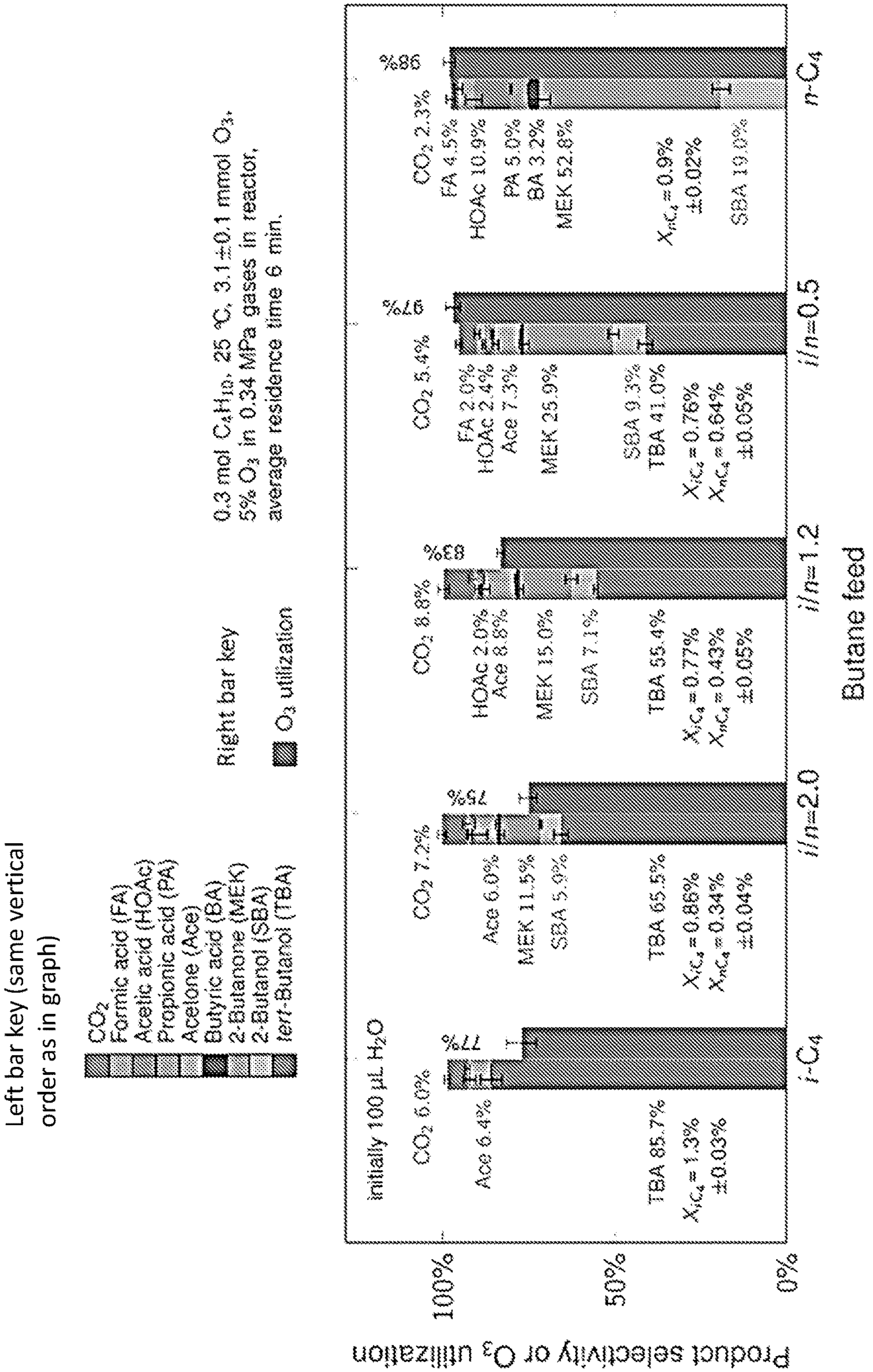

FIG. 1B

ACTIVATION OF ALKYL SUBSTRATES IN CONDENSED PHASE WITH OZONE

CROSS-REFERENCE TO RELATED APPLICATIONS

The present application claims priority to U.S. Provisional Patent Application No. 63/327,531 that was filed Apr. 5, 2022, the entire disclosure of which is hereby incorporated by reference.

REFERENCE TO GOVERNMENT RIGHTS

This invention was made with government support under 2119754 awarded by the National Science Foundation. The government has certain rights in the invention.

BACKGROUND

Most reported technologies of selective oxidation of alkanes suffer from low yields of liquid oxygenates. At the generally higher temperatures (50-200° C.) required to oxidize alkanes with $O_2$, the substrate and products suffer appreciable combustion to form $CO_2$, a greenhouse gas. The direct dehydrogenation of alkanes requires even higher temperatures (>450° C.) to produce olefins at low single-pass conversions. Ozone has been shown to be a powerful oxidant for some hydrocarbon materials, but it is challenging to effectively utilize ozone towards any particular reaction product as well as to minimize over-oxidation to $CO_2$ and ozone decomposition.

SUMMARY

Provided herein are processes for the ozonation of alkyl substrates, including linear alkanes in the liquid phase. The present processes make use of a branched alkane activator, and generally, a protic additive. These processes are based, at least in part, on the unexpected finding that the branched alkane activator can be used to tune product selectivity, limit overoxidation to CO and $CO_2$, and increase ozone utilization. Moreover, the ability to add the branched alkane activator and the protic additive to the condensed phase to control reaction pathways is a distinct advantage of the present processes over gas phase ozonations.

An embodiment of a process for oxidizing an alkyl substrate comprises combining an alkyl substrate and ozone in a liquid phase medium comprising a branched alkane activator and a protic additive under conditions sufficient to oxidize the alkyl substrate to products, wherein the alkyl substrate is selected from linear and cyclic alkanes.

An embodiment of a process for oxidizing a linear alkane comprises combining the linear alkane and ozone in a liquid phase medium comprising a branched alkane activator and a protic additive under conditions sufficient to oxidize the linear alkane to products, wherein the liquid phase medium is free of added $CO_2$, and the process further comprises adding the protic additive to the liquid phase medium prior to oxidizing the linear alkane.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

FIG. 1B plots product distribution and ozone utilization in the ozonation of various n-butane (n-$C_4$ or n)/isobutane (i-$C_4$ or i) mixtures with the addition of 100 μL water. The reaction conditions for FIGS. 1A-1B were as follows: 25° C., 3.1±0.1 mmol $O_3$, 0.34 MPa $O_3$+$O_2$+Ar partial pressure, average residence time~6 min. It is noted that "i/n=x" represents a mixture with isobutane/n-butane molar ratio of x.

DETAILED DESCRIPTION

Figure 1A:
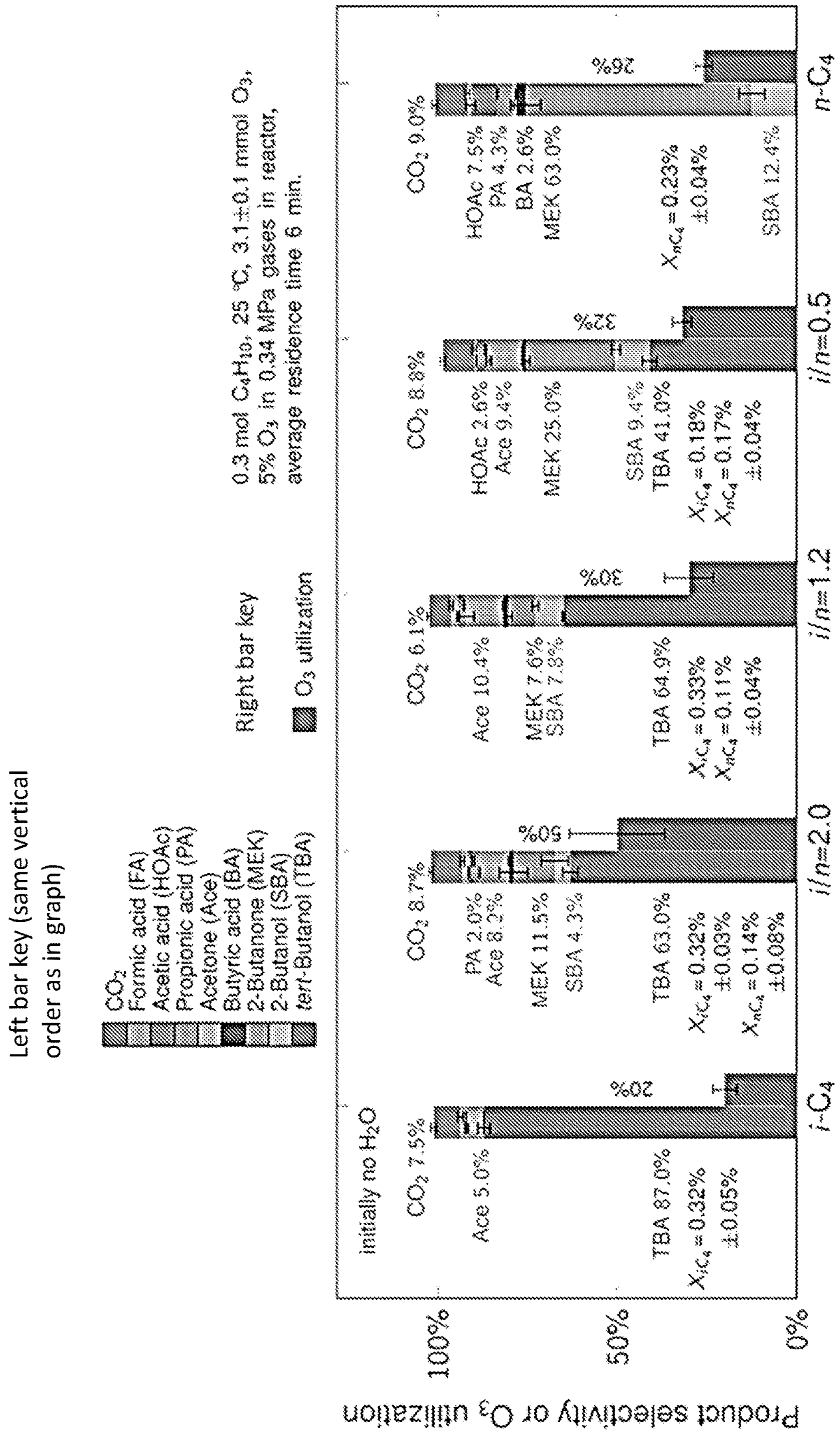
FIG. 1A plots product distribution and ozone utilization in the ozonation of various n-butane (n-$C_4$ or n)/isobutane (i-$C_4$ or i) mixtures without the addition of any water.

Provided herein are processes for the ozonation of alkyl substrates, including linear alkanes in the liquid phase. By "liquid phase" it is meant that the relevant reactions take place in the liquid phase, at a liquid-liquid interface, as opposed to the gas phase. The processes involve combining the desired alkyl substrate with ozone in a liquid phase medium comprising a branched alkane activator.

The present processes may be used to oxidize alkyl substrates. The alkyl substrates include linear alkanes. The class of linear alkanes refers to saturated hydrocarbons in which all of the carbons are in an unbranched (linear) chain. The linear alkanes are generally unsubstituted, i.e., comprising only hydrogen and carbon. The linear alkane may have various numbers of carbons, e.g., at least 2, 3, 4, 5, or 6 carbons, or from 2 to 15 carbons. Illustrative linear alkanes include ethane, propane, n-butane, pentane, hexane, heptane, octane, etc. Linear alkanes are distinguished from branched alkanes (including the present branched alkane activators) as well as cyclic alkanes. A single type or a combination of different types of linear alkanes may be used. That is, the alkyl substrate being oxidized may be a single type of linear alkane or a combination of different types of linear alkanes. The linear alkane(s) may be provided as a feedstock comprising other components which may be inherently present due to the particular source of the feedstock. An illustrative feedstock is a natural gas liquid feedstock, which may be derived from shale gas or natural gas.

In embodiments, the alkyl substrate is a cyclic alkane. The cyclic alkane may have various numbers of carbons, e.g., at least 5, 6, 8, 9, 10, carbons, or from 6 to 16 carbons. Illustrative cyclic alkanes include cyclohexane, cyclooctane, and cyclodecane. The cyclic alkanes are generally unsubstituted, i.e., comprising only hydrogen and carbon. Other cyclic alkanes may be used, including those having various numbers of carbon atoms as described above for the linear alkanes.

In embodiments, the alkyl substrate consists of one or more linear alkanes. In embodiments, the alkyl substrate consists of propane, n-butane, or both.

The present processes make use of a branched alkane activator. As demonstrated in the Example, below, it has been unexpectedly found that the branched alkane activator can be used to tune selectivity for a desired oxidation product. This includes favoring the formation of alcohols (or a specific alcohol) as well as greatly suppressing oxidation to other products (e.g., ketones, acids) and/or to $CO_2$. Without wishing to be bound to any particular theory, it is believed that ozone may preferentially attack the branched alkane activator to form a hydrotrioxide intermediate, thereby serving as an ozone trap that limits the overutilization of ozone towards other reaction products.

The branched alkane activator is a saturated hydrocarbon having one or more alkyl groups bound to a linear carbon chain. The branched alkane activators are generally unsubstituted, i.e., comprising only hydrogen and carbon. The branched alkane activator may have various numbers of carbons, e.g., from 4 to 20. This includes from 4 to 18, from 4 to 16, from 4 to 14, from 4 to 12, from 4 to 10, and from 4 to 8. The branched alkane activator desirably comprises a tertiary carbon. The branch in the branched alkane activator may be at a terminal carbon; that is, at least one of the alkyl groups that is bound to the linear carbon chain of the branched alkane activator is bound to a terminal carbon of the chain. The branched alkane activator is a different chemical compound than the alkyl substrate being oxidized in the process. The branched alkane activator is generally in its liquid form under the conditions being used in the process. In embodiments, the branched alkane activator is an isoalkane, e.g., isobutane.

The present processes also generally make use of a protic additive. The protic additive is a compound that is capable of hydrogen bonding by comprising at least one hydrogen atom bound to an electronegative atom. Desirably, the protic additive is capable of stabilizing the hydrotrioxide intermediate derived from the branched alkane activator (described above) via hydrogen bonding. The protic additive is generally in its liquid form under the conditions being used in the process. In embodiments, the protic additive has a $pK_a$ in water at room temperature (20° C. to 25° C.) of greater than 3, 4, 5, 6, 7, 8, 9, 10, etc. The $pK_a$ may be as high as 16, the $pK_a$ of tert-butyl alcohol. Illustrative protic additives include water and alcohols. The alcohol may be a short chain alcohol having from 1 to 6 carbons, from 1 to 5 carbons, or from 1 to 4 carbons, e.g., methanol, ethanol, isopropanol, tert-butyl alcohol. In embodiments, the protic additive is not a carboxylic acid such as formic acid, acetic acid, propionic acid, or butyric acid; in such embodiments, the liquid phase medium is free of these components. In embodiments, the protic additive is not a strong acid such as sulfuric acid or a super acid having an acidity stronger than sulfuric acid; in such embodiments, the liquid phase medium is free of these components. The protic additives are desirably distilled to eliminate the presence of certain impurities; in such cases, the protic additive may be referred to as a "distilled protic additive." A single type or combinations of different types of protic additives may be used.

The protic additive generally refers to a compound which is added to the liquid phase medium prior to carrying out the ozonation. This is in contrast to the protic additive being a product of the ozonation (e.g., $H_2O$ or an alcohol). In embodiments, the protic additive is not a product of the ozonation. In embodiments, the protic additive is not an alcohol, e.g., tert-butyl alcohol, produced by the ozonation. In embodiments, the present process comprises adding any of the disclosed protic additives to the liquid phase medium prior to the ozonation to produce a product from the alkyl substrate.

In the present processes, the ozone may be provided as a feed gas mixture, e.g., $O_3$ in $O_2$ or $O_3$ in air. An inert gas, e.g., $N_2$, Ar, etc., may be included in the feed gas mixture. This is useful to keep a vapor phase present above the liquid phase medium outside of its flammability envelop at the temperature and pressure being used in the process and to avoid toxicity.

Although no catalyst is required for the present processes, in other embodiments, a catalyst may be used. If a catalyst is used, the catalyst may contain transition metals or their combinations, such as a first-row transition metal (e.g., Fe, Co, Ni) and/or a platinum group metal, e.g., Pd, Pt. The catalyst may be supported transition metal catalyst in which the selected transition metal is incorporated into or deposited on a surface of a metal oxide substrate, e.g., an oxide of aluminum, silicon, titanium, magnesium, cerium, zirconium, etc. or two-dimensional materials such as graphene or hexagonal boron nitride. Illustrative metal oxide substrates include silicate and zeolite. Mesoporous silicates such as KIT-5, KIT-6, SBA-16, TUD-1 may be used.

As described above, the ozonation reaction is carried out in the liquid phase medium. The liquid phase medium comprises the selected alkyl substrate, the branched alkane activator, the ozone (at least some of the ozone of the feed gas mixture becomes dissolved in the liquid phase medium), and generally, the protic additive. The selected alkyl substrate may be a liquid under the conditions being used in the process. However, in other embodiments, the selected alkyl substrate may not be a liquid and/or may not be dissolved (or only partially dissolved) in the liquid phase medium under the conditions being used in the process. The catalyst, if present, may either be dissolved or suspended in the liquid phase medium, contained in baskets that allow the liquid phase medium to pass through, or fluidized in a fraction of the reactor. In embodiments, the liquid phase medium comprises (or consists of) the alkyl substrate to be oxidized, the branched alkane activator, the ozone, the protic additive, and optionally, a catalyst. However, such embodiments also encompass the presence of the resulting products of the ozonation in the liquid phase medium.

The present processes do not require the use of carbon dioxide ($CO_2$). Thus, at least in embodiments, the liquid phase medium is free of, i.e., does not comprise, $CO_2$ (whether the $CO_2$ is in its gaseous or liquid state). These embodiments refer to the absence of any $CO_2$ (whether the $CO_2$ is in its gaseous or liquid state) separately added to the liquid phase medium. These embodiments, however, do not preclude the formation of an amount of $CO_2$ as a product of ozonation. However, if any $CO_2$ is present in the liquid phase medium as a product of ozonation, it is generally present at an amount of less than 0.4 mol %. This includes less than 0.3 mol %, less than 0.2 mol %, less than 0.1 mol %, less than 0.05%, and less than 0.01%. This includes from 50 ppm to 0.4 mol %.

The present processes may be carried out in a variety of reactor systems, including batch reactor systems, semi-continuous flow reactor systems, and continuous flow reactor systems. When a solid catalyst is used, the processes may be carried out in fixed-bed and fluidized bed systems. Reactor systems in which gas (e.g., feed gas mixture) and liquid (e.g., alkane/branched alkane activator/protic additive) phases may be continuously admitted and withdrawn are useful to maximize $O_3$ utilization and yield of certain reaction products. It is noted that for semi-continuous and continuous reactor systems, the addition of the protic additive prior to the ozonation may refer to an initial addition of the protic additive to the liquid phase medium. In such embodiments, subsequent to the initial addition, the protic additive may be continuously or intermittently added to the liquid phase medium. In other such embodiments, subsequent to the initial addition, no further protic additive is added to the liquid phase medium.

The conditions used in the present processes to induce oxidation of the alkyl substrate refer to parameters such as the temperature, the total pressure, as well as others further described below. The temperatures and total pressures used are generally mild. In embodiments, the temperature is at least 15° C. However, higher temperatures may be used, e.g., at least 100° C., at least 130° C. Illustrative temperatures include those in a range of from 15° C. to 130° C., 15° C. to 60° C., 15° C. to 50° C., 15° C. to 40° C., 15° C. to 30° C., and 15° C. to 25° C. The total pressure refers to the total pressure of the vapor phase present above, and in contact with, the liquid phase medium at the selected temperature. This vapor phase comprises ozone, as well as any other gases present in the gas mixture used to deliver the ozone, e.g., $O_2$, air, an inert gas, or combinations thereof. The vapor phase may also comprise some amount of the vapor form of the selected alkyl substrate and/or the selected branched alkane activator. In embodiments, the total pressure is less than 5 MPa, less than 3 MPa, or less than 1 MPa. Illustrative total pressures include those in a range of from 0.45 MPa to 5 MPa, from 0.45 MPa to 3 MPa, and from 0.45 MPa to 1 MPa. The main criterion is that the temperature is below the critical temperature of the selected feed hydrocarbon mixture such that condensation by application of mild pressure is possible.

The conditions also refer to the amount of the branched alkane activator being used. The amount may be given in terms of an activator-to-alkyl substrate mole ratio of (moles of branched alkane activator)/(moles of alkyl substrate being oxidized). The amount is generally selected to achieve a desired selectivity for a certain product, including maximizing the selectivity of an alcohol while minimizing the selectivity of an acid, a ketone, and/or $CO_2$. In embodiments, the activator-to-alkyl substrate mole ratio is greater than 0.2, greater than 0.5, greater than 1, greater than 1.5, or greater than 2. This includes an activator-to-alkyl substrate mole ratio in a range of from 0.2 to 10, from 0.2 to 8, from 0.2 to 6, from 0.2 to 4, from 0.2 to 2, and from 0.2 to 1. If more than a single type of alkyl substrate used, the alkyl substrate molar amount refers to the total molar amount of alkyl substrate. As demonstrated in Example 1, below, adding isobutane as a branched alkane activator during the ozonation of propane reduces $CO_2$ selectivity from about 66% (no isobutane) to less than 9% (at an activator-to-alkane mole ratio of 2). (See FIG. 3.) This is a remarkable and unexpected drop in $CO_2$ selectivity.

The conditions also refer to the amount of the protic additive being used. The amount is generally selected to maximize $O_3$ utilization, which may be quantified as the number of moles of a certain reaction product (e.g., alcohol)/moles of ozone fed. (Also see the definitions in Examples 1 and 2, below.) Illustrative amounts of protic additive include at least 0.1 mol %, at least 0.5 mol %, at least 5 mol %, at least 10 mol %, or at least 50 mol %. In embodiments, the amount is in a range of from 0.1 to 50 mol %, 1 to 50 mol %, 10 to 50 mol %, or 1 to 5 mol %. The amount of the protic additive in the liquid phase medium may also be referred to as a volume % of the total volume of the liquid phase medium. In embodiments, the amount is in a range of from 0.2 volume % to 50 volume %, 0.2 volume % to 25 volume %, 0.2 volume % to 15 volume %, 0.2 volume % to 10 volume %, 0.2 volume % to 5 volume %, from 0.2 volume % to 2 volume %, from 0.2 volume % to 1.5 volume %, or from 0.2 volume % to 1 volume %. The balance of the liquid phase medium may be composed of the liquid alkyl substrate(s) (with ozone and any catalyst, if present, dissolved therein). As demonstrated in Example 1, below, $O_3$ utilization in n-butane oxidation was in a range of from 20% to 50% in the absence of water (FIGS. 1A and 2A), but increased to a range of from 75% to 98% in the presence of water (otherwise using the same conditions) (FIGS. 1B and 2B).

The conditions also refer to the partial pressure of non-condensable gases in the vapor phase present above, and in contact with, the liquid phase medium at the selected temperature and total pressure. For example, if the feed gas mixture comprises $O_3$, $O_2$, and an inert gas, the partial pressure of non-condensable gases refers to the pressure of these three gases. The partial pressure is generally selected to maximize $O_3$ utilization. Illustrative partial pressures include from 0.02 MPa to 0.24 MPa, from 0.1 MPa to 0.6 MPa, from 0.2 MPa to 0.5 MPa, and from 0.2 MPa to 0.4 MPa.

The conditions also refer to the mole fraction of ozone in the feed gas mixture. For example, if the feed gas mixture comprises $O_3$ in $O_2$ and inert gas, the mole fraction refers to the $O_3/(O_3+O_2+\text{inert gas})$ mole fraction. The mole fraction is generally selected to maximize $O_3$ utilization. Illustrative mole fractions of ozone include from 1% to 5%, 1.5% to 4.5%, from 2% to 4%, these concentrations being at safe ozone levels.

The products obtained from the ozonation depend upon the selected alkyl substrate as well as the conditions used. Example 1 below lists possible products from the ozonation of n-butane and propane. The present processes may further comprise collecting one or more of the products produced. Other steps include using the collected products, e.g., in chemical reactions to form other products. For example, products such as tert-butyl alcohol and isopropanol are precursors for major commodity chemicals. In particular, propene can be accessed from isopropanol by dehydration, which is significantly less energy intensive compared to direct dehydrogenation of propane.

The present processes may be characterized by a selectivity for a particular product. By selectivity, it is meant ((moles of particular product)/(total moles of products obtained))*100. (Also see the definitions in Examples 1 and 2, below.) In embodiments, the selectivity of alcohol products is at least 50%, at least 60%, at least 70%, or at least 80%. This may refer to all types of alcohol products (or a single type of alcohol) generated in the process. In embodiments, the selectivity of acid products is no more than 10%, no more than 8%, no more than 6%, or no more than 4%. This may refer to all types of acid products (or a single type of acid) generated in the process. In embodiments, the selectivity of ketone products is no more than 40%, no more than 30%, no more than 20%, or no more than 15%. This may refer to all types of ketone products (or a single type of ketone) generated in the process. In embodiments, the $CO_2$ selectivity is no more than 20%, no more than 10%, or no more than 5%.

The present processes may be characterized by a $O_3$ utilization value as defined above. In embodiments, the $O_3$ utilization value is at least 70%, at least 80%, at least 90%, or at least 95%.

The selectivities and $O_3$ utilization values described above may be reported with reference to a particular set of conditions used in the process.

EXAMPLES

Example 1

Introduction

Light alkanes such as ethane, propane, butanes and pentanes are collateral products of shale gas extraction. The increased production of shale gas in the United States makes these hydrocarbons relatively inexpensive feedstocks for making value-added chemicals as opposed to being either flared or burned as fuel, both of which result in greenhouse gas emissions. This Example demonstrates a technology to selectively oxidize linear light alkanes with ozone to liquid oxygenates at ambient temperature and mild pressures. The linear alkane to be oxidized was condensed as liquid either alone or along with a certain fraction of isobutane at ambient temperature and mild pressures. The resulting liquid phase was then mixed with ozone. The concentration of ozone in the liquid phase was tuned by varying the partial pressure of ozone in the gas phase of a closed vessel while keeping the overall concentration of alkanes in the gas phase above the upper flammability limit. Under these conditions, the mixed alkanes underwent oxidation in the liquid phase to form oxygenated products at >90% selectivity (defined as the mole fraction of oxygenated liquid products relative to all products formed). When n-butane and isobutane were co-fed, the major oxygenated products included tert-butyl alcohol, sec-butyl alcohol, methyl ethyl ketone, acetone, acetic acid, formic acid, and propionic acid, with tert-butyl alcohol being the dominant product. $CO_2$ was also formed as product with its selectivity (fraction of $CO_2$ formed relative to all products) being <10%. With n-butane alone as feed at otherwise identical conditions, tert-butyl alcohol was not formed and the ozone utilization was much lower (i.e., more ozone was lost to decomposition rather than forming the oxygenated products). When water was added to the feed mixture, the ozone utilization increased with concurrent increases in alkane conversions and selectivity towards oxygenated products, with even less $CO_2$ formation. The beneficial effects of adding isobutane and water were even more pronounced with a mixed feed of propane and isobutane. With only propane in the feed, the $CO_2$ formation was dominant with its selectivity exceeding 60% even in the presence of water. When an equimolar amount of isobutane was added to propane in the feed, both the ozone utilization and the liquid oxygenate selectivity approached approximately 90%, with the $CO_2$ formation being significantly reduced. The major products of propane oxidation when isobutane was present included tert-butyl alcohol, isopropyl alcohol, acetone, and formic acid.

Experimental

Chemicals

The dioxygen (UHP Plus), argon (HP), propane (UHP), n-butane (UHP), and isobutane (UHP) were all purchased from Matheson.

Semi-Batch Runs

The experimental apparatus has been described in Zhu, H., et al. *ACS Sustainable Chem. Eng.* 2021, 9 (16), 5506-5512. The dioxygen stream was used to generate ozone by an Atlas Ozone Generator and then was mixed with argon in a reservoir. (Lundin, M. D., et al. *ACS Sustainable Chem. Eng.* 2015, 3 (12), 3307-3314.) Briefly, a Teflon-lined Parr vessel was evacuated at 80° C. under vacuum prior to charging the desired amounts of liquid alkanes from an ISCO syringe pump cooled to 10° C. An option to direct the liquid alkane stream through a sample loop containing distilled water was provided to meter in controlled amounts of water. The reactor stirrer was set at 1000 rpm. Throughout a semi-batch run, an $O_2/O_3/Ar$ mixture was supplied via a pressure regulator maintained at a constant pressure, and this gas mixture passed through the reactor continuously. The alkanes that escaped with the gas phase were partially condensed in a cold trap held around −60 to −50° C. and ambient pressure to concentrate the $CO_2$. The gas from the condenser was collected in Tedlar sample bags. At the end of a run, the reactor was placed in an ice bath kept in a walk-in freezer at −18° C. At this temperature, the vapor pressure of all compounds remaining in the reactor was much reduced. Then a weighed amount of cold methanol was added into the reactor, and the volatile alkanes were allowed to vaporize at 0-4° C. and condensed in the cold trap. The trap was maintained either around −60 to −50° C. for butanes, or around −90° C. when propane was present. After adding 2-pentanone as an internal standard, the methanolic liquid sample was injected into a GC equipped with a HP-PLOT/Q column to resolve $\geq C_2$ products and a flame ionization detector (FID). The methanolic liquid sample was also added to $D_2O$ with maleic acid as an internal standard to quantify formic acid by $^1$H NMR. The gas samples collected in tedlar bags were injected into another GC equipped with a thermal conductivity detector to analyze the $CO_2$ and an FID to analyze the hydrocarbons.

Definitions

As butane oxidation is limited by the quantity of ozone, and the majority of the butanes are condensed during/after reaction (i.e., minor loss of the most volatile components), their conversions $X_{iC_4}$ and $X_{nC_4}$ were estimated from the total product yields from isobutane and n-butane ozonation as follows.

$$\frac{n_{iC_4,prod}}{n_{iC_4,0}} < X_{iC_4} < \frac{n_{iC_4,prod} + \frac{1}{4}n_{C_1}}{n_{iC_4,0}},$$

$$\frac{n_{nC_4,prod}}{n_{nC_4,0}} < X_{nC_4} < \frac{n_{nC_4,prod} + \frac{1}{4}n_{C_1}}{n_{nC_4,0}}.$$

Here $n_{iC_4,0}$ and $n_{nC_4,0}$ are the initial quantities of isobutane and n-butane, respectively. It is clear that tert-butyl alcohol and acetone form predominantly from isobutane, and that 2-butanol, 2-butanone, butyric acid, propionic acid, and acetic acid form predominantly from n-butane. The total quantities of isobutane and n-butane converted to these products are $n_{iC_4,prod}$ and $n_{nC_4,prod}$, respectively.

$$n_{iC_4,prod} = n_{tert-butanol} + n_{acetone},$$

$$n_{nC_4,prod} = n_{sec-butanol} + n_{butanone} + n_{butyric\ acid} + n_{propionic\ acid} + \frac{1}{2}n_{acetic\ acid}.$$

However, both isobutane and n-butane ozonation may form formic acid and $CO_2$, which are the $C_1$ minor products (total quantity is $n_{C_1}$). Thus, the upper and lower bounds for the conversions were estimated with the inequalities and then averaged to estimate the deviation shown in the figures.

$$n_{C_1}=n_{formic\ acid}+n_{CO_2}.$$

In contrast to butane mixtures, acetone, formic acid, and $CO_2$ are the three common products from both alkanes during the ozonation of isobutane and propane mixtures. These products with uncertain sources contribute to a significant fraction of the carbons in the products. Therefore, only the total conversion of alkanes $X_{C_xH_y}$ was estimated as follows.

$$\frac{n_{C_xH_y,prod}}{n_{C_xH_y,0}} < X_{C_xH_y} < \frac{n_{C_xH_y,prod} + \frac{1}{3}n_{C_1}}{n_{C_xH_y,0}}.$$

Here $n_{C_1}$ still denotes the total amounts of formic acid and $CO_2$. $n_{C_xH_y,0}$ is the total amount of alkanes initially charged into the reactor. $n_{C_xH_y,prod}$ is the estimated amount of converted alkanes based on the products, excluding $C_1$ products.

$$n_{C_xH_y,prod}=n_{tert-butanol}+n_{iso-butanol}+n_{isobutyraldehyde}+n_{iso-propanol}+n_{acetone}$$

For neat propane, the propane conversion was estimated by $$X_{C_3H_8} = \frac{n_{iso-propanol} + n_{acetone} + \frac{1}{3}n_{C_1}}{n_{C_3H_8,0}}.$$

The product selectivity for compound i is defined as follows, where the denominator is the total amount of all products.

$$S_i = \frac{n_i}{\sum_j n_j}$$

The product distribution is complex in the case of $iC_4+C_3$ mixed feed compared to only isobutane as feed when only three major products form. Therefore, a different definition was adopted for ozone utilization as follows, in order to compare the total amount of electron transfer initiated per mole of ozone. It should be noted that no reaction was observed with only dioxygen (i.e., without any ozone). However, in the presence of ozone, the dioxygen present in the mixture may be involved in the oxidation of radical intermediates at the conditions studied.

$$U = \frac{\text{quantity of electron transfered to oxidants}}{4\times(\text{quantity of } O_3 \text{ introduced})} = \frac{n_e}{4n_{O_3}}$$

$$n_e=2n_{tert-butanol}+2n_{sec-butanol}+4n_{butanone}+3n_{acetone}+6n_{butyric\ acid}+5n_{propionic\ acid}+5n_{acetic\ acid}+5n_{formic\ acid}+7n_{CO_2}$$

In the experiment, the cold trap and its contents were weighed directly to estimate the amount of condensed alkanes. The carbon balance is defined as follows. Per this definition, the C balance values in all experiments were in 94-99% range.

$$C = \frac{\text{amount of carbons in(condensed alkanes + products + gas samples)}}{\text{amount of carbons charged into reactor}}$$

$$\text{amount of carbons in products}=4n_{tert-butanol}+4n_{sec-butanol}+4n_{butanone}+3n_{acetone}+4n_{butyric\ acid}+3n_{propionic\ acid}+2n_{acetic\ acid}+n_{formic\ acid}+n_{CO_2}$$

Results and Discussion

Ozonation of Mixtures of n-Butane and Isobutane

Several mixtures of the butanes with different compositions, as well as neat n-butane, were treated with ozone at (25.0±0.6) ° C. to evaluate the effect of butane composition on the observed products. It was noted that the i/n ratio of 1.2 simulates the $C_4$ composition in a natural gas sample. The experiments were performed with either 100 μL water addition or no initial water addition (water is an expected product of some ozonation reactions).

The major products from isobutane ozonation were tert-butyl alcohol, acetone, formic acid, and carbon dioxide, with negligible formation of iso-butyl alcohol, isobutyraldehyde and tert-butyl hydroperoxide. n-Butane alone as feed produced a complex oxygenate mixture including 2-butanol, 2-butanone, butyric acid, propionic acid, acetic acid, and formic acid, accompanied by carbon dioxide. Small quantities of a hydroperoxide (most likely 2-hydroperoxylbutane) and acetone also formed.

Figure 2A:
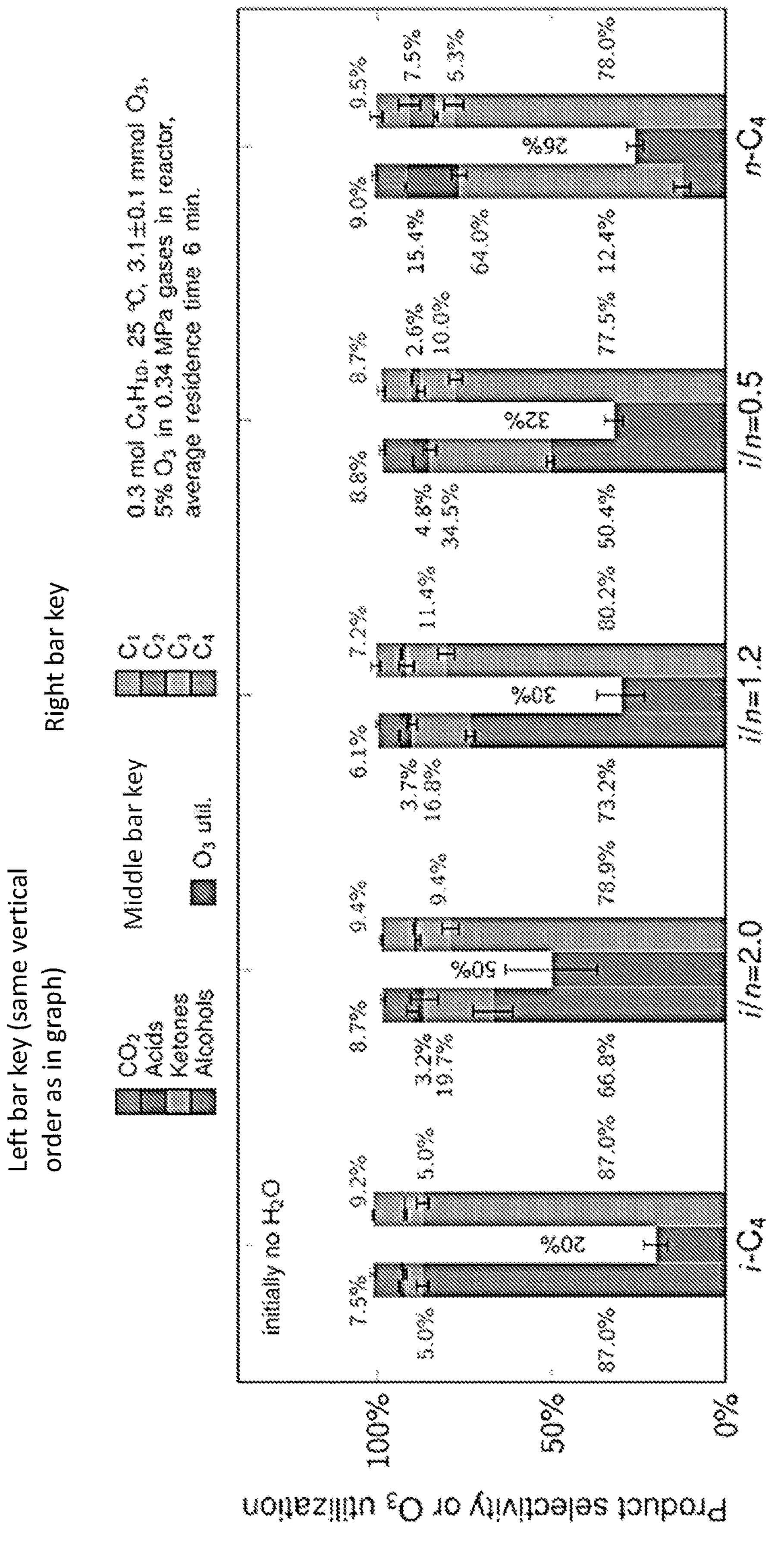
FIG. 2A plots product distribution (grouped by either the product types or the number of carbons in a molecule) and ozone utilization in the ozonation of various n-butane (n-$C_4$ or n)/isobutane (i-$C_4$ or i) mixtures without the addition of any water.
Figure 2B:
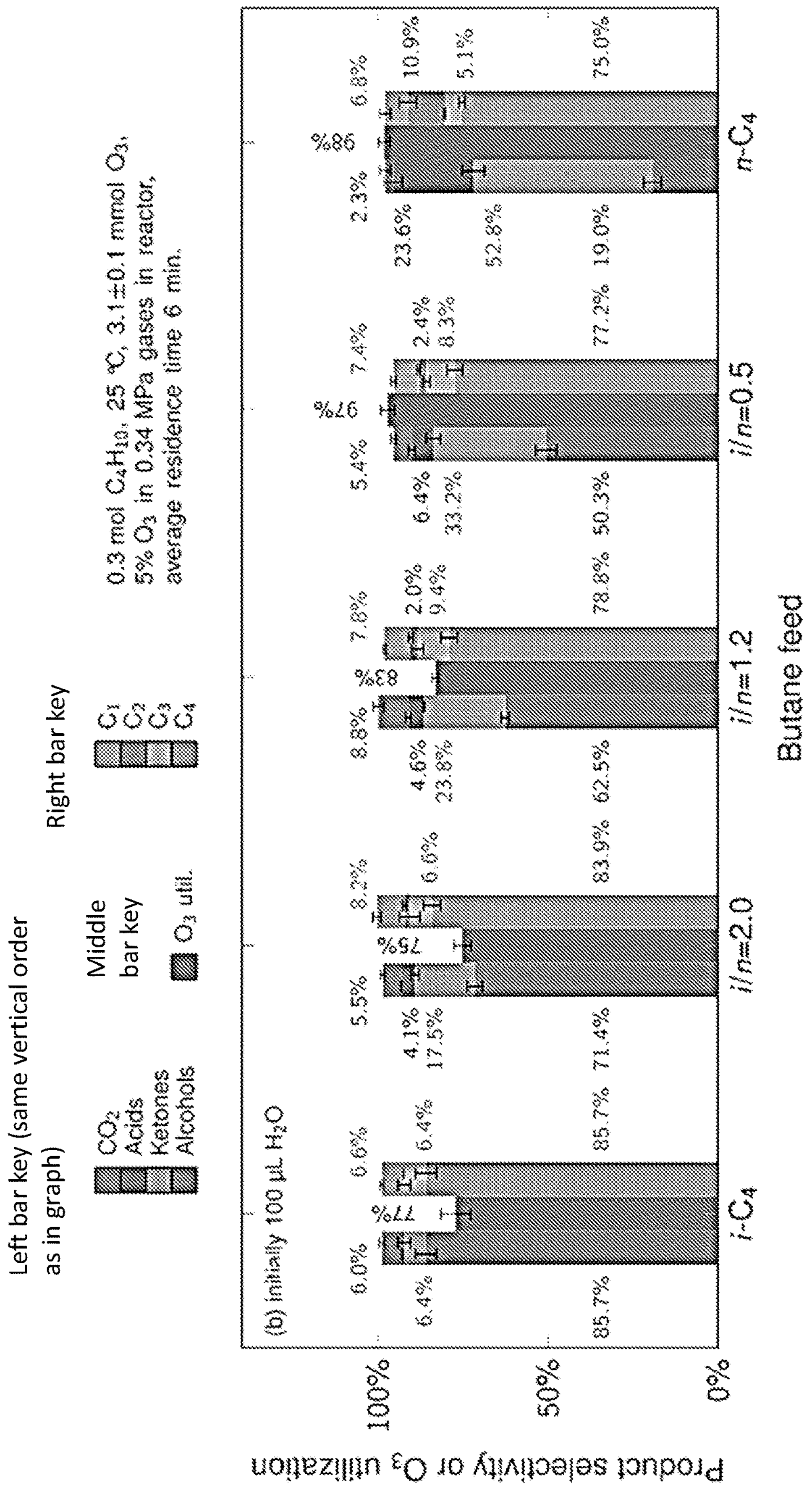
FIG. 2B plots product distribution (grouped by either the product types or the number of carbons in a molecule) and ozone utilization in the ozonation of various n-butane (n-$C_4$ or n)/isobutane (i-$C_4$ or i) mixtures with the addition of 100 μL water.

Along with butane conversions and ozone utilization, FIGS. 1A-1B show detailed product distributions, while FIGS. 2A-2B show products grouped by either their types or the number of carbons in a molecule. The sharp differences in the values of butane conversion and ozone utilization without (FIG. 1A) and with initial water addition (FIG. 1B) confirmed the enhancement of reactivity when 100 μL water was initially added to the feed mixture. The increases in ozone utilization and ketone selectivity with increasing n-butane fraction in the feed suggests that 2-butanol is highly reactive with ozone, as its further oxidation to 2-butanone consumed more ozone than oxidation to an alcohol. In contrast, tert-butyl alcohol is fairly stable in the presence of ozone. Increasing the fraction of n-butane in the $C_4$ feed mixture favored C═O formation and C—C cleavage (FIGS. 2A-2B). While the resulting water byproduct should also favor ozonation, the byproduct amount was rather small compared to the initially added water.

The progressive increase in isobutane content in the mixed $C_4$ feed tuned the product distribution. Compared to the run with neat n-butane, isobutane addition suppressed the formation of acids (including acetic acid and propionic acid from C—C cleavage in 2-butanone). Also, the ratio of 2-butanone/2-butanol decreased as more isobutane was introduced into the butane mixture, indicating that isobutane may intercept ozone to preferentially form TBA, thereby preventing further oxidation of the alcohol to ketone by ozone.

Mixtures of Isobutane and Propane

Mixtures of isobutane and propane were also evaluated to investigate if isobutane addition has a beneficial effect on propane ozonation as well. Unlike $C_4$ mixtures, the vapor pressures of $C_3$+i$C_4$ alkane mixtures vary substantially in the range of feed compositions studied (0.56-0.98 MPa). The reactor was pressurized with $O_3$+$O_2$+Ar mixtures such that the $O_3$ partial pressure was nearly the same in all cases.

Figure 3:
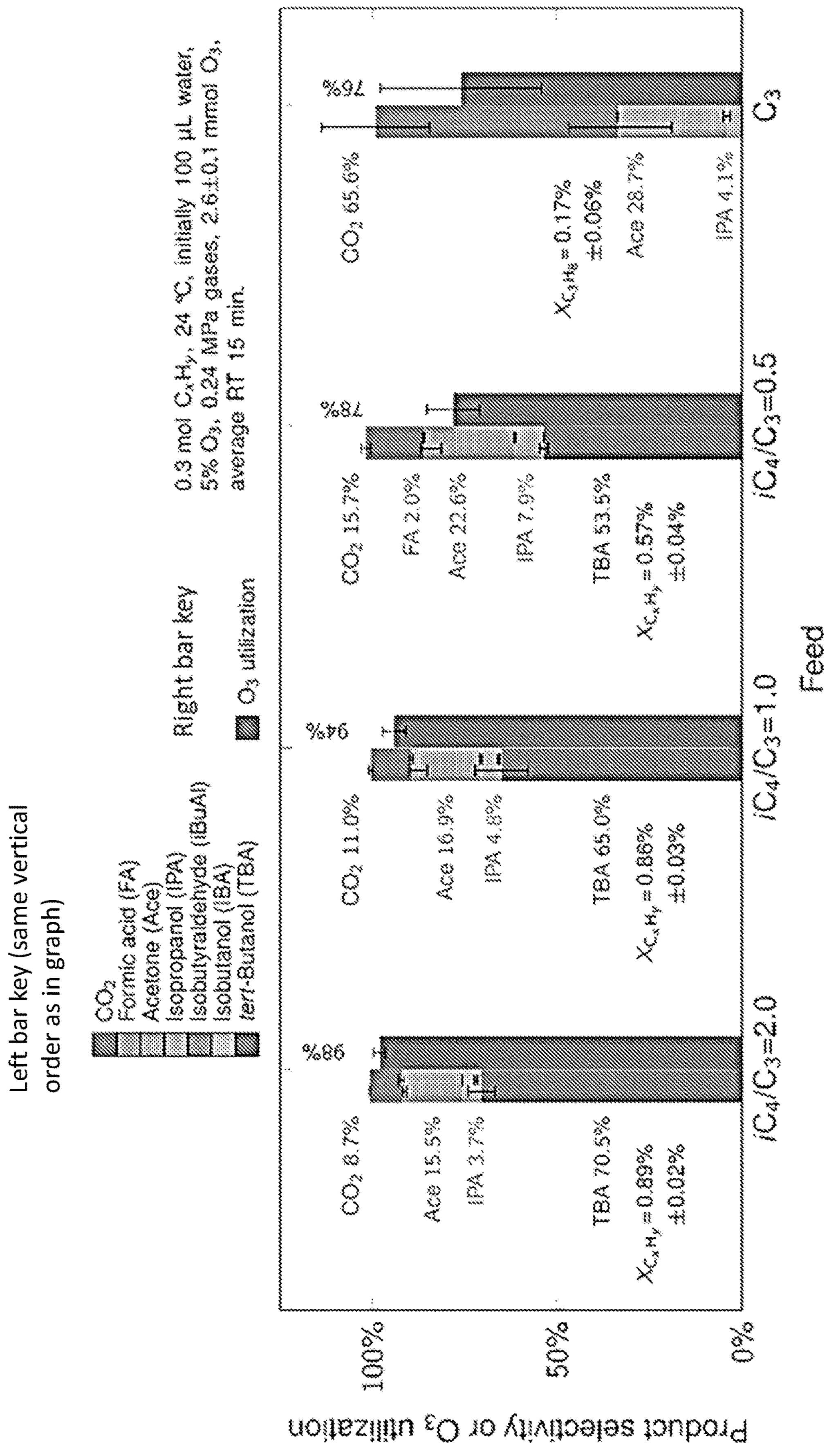
FIG. 3 plots product distribution and ozone utilization in the ozonation of various n-butane (n-$C_4$ or n)/propane ($C_3$) mixtures with the addition of 100 μL water.

As shown in FIG. 3, the addition of isobutane (isobutane/propane=0.5 mol/mol) doubled the isopropanol yield compared to neat propane and significantly inhibited the over-oxidation of oxygenates to $CO_2$. With only propane in the feed, the $CO_2$ selectivity was ~66%. Adding 33 mole % isobutane diminished the $CO_2$ selectivity to ~16%, while increasing the overall hydrocarbon conversion. At 66 mole % isobutane in the feed, the $CO_2$ selectivity dropped even further to ~9%. Although the net oxidizing equivalents from ozone were similar in each case, ozone utilization was drastically shifted toward the desired oxygenate formation. The increased formation of isopropanol in the presence of isobutane at mild conditions suggests a potential low energy route for making propene from propane. Since acetone forms from both propane and isobutane, the quantity of acetone produced from isopropanol oxidation is unclear. Since formic acid and $CO_2$ are byproducts of acetone formation from isobutane, it may be inferred that for isobutane/propane ratios of 1-2, at least one third of the acetone forms from propane.

Conclusions

The foregoing results demonstrate an efficient method for activating linear alkanes in their condensed liquid phase at mild pressures and conditions with the aid of isobutane. The product yields may be further optimized by fine-tuning the reaction conditions (isobutane content in feed, $O_3$ partial pressure, and protic additives, in particular) to maximize ozone utilization and the yield of valuable liquid oxygenates. The results indicate that increasing isobutane content in the mixed alkane feed dictates product selectivity, by (a) tuning the ozone availability in the liquid phase, and (b) preferentially utilizing ozone to form active intermediates that not only promote the formation of tertiary butyl alcohol but also convert the linear alkanes in the feed to liquid oxygenates, while minimizing $CO_2$ formation. The demonstrated concept may be used to convert stranded natural gas liquids to valuable oxygenates.

Example 2

Introduction

This Example demonstrates the oxidation of mixed alkanes (propane, n-butane, and isobutane), by ozone in a condensed phase at ambient temperature and mild pressures (up to 1.3 MPa). Oxygenated products such as alcohols and ketones are formed with a combined molar selectivity of >90%. The ozone and dioxygen partial pressures are controlled such that the gas phase is always outside the flammability envelope. Because the alkane-ozone reaction predominantly occurs in the condensed phase, the unique tunability of ozone concentrations in hydrocarbon-rich liquid phases can be harnessed for facile activation of the light alkanes, while also avoiding over oxidation of the products. Further, adding isobutane and water to the mixed alkane feed significantly enhances ozone utilization and the oxygenate yields. The ability to tune the composition of the condensed media by incorporating liquid additives to direct selectivity is a key to achieving high carbon atom economy, which cannot be achieved in gas phase ozonations. Even in the liquid phase, without added isobutane and water, combustion products dominate during neat propane ozonation with $CO_2$ selectivity being >60%. In contrast, ozonation of a propane+isobutane+water mixture suppresses $CO_2$ formation to 15% and nearly doubles the yield of isopropanol. A kinetic model based on formation of a hydrotrioxide intermediate can adequately explain the yields of the observed isobutane ozonation products. Estimated rate constants for the formation of oxygenates establish that the demonstrated concept may be used for facile and atom-economic conversion of natural gas liquids to valuable oxygenates.

Methods

Materials

The dioxygen (UHP Plus), argon (HP), propane (UHP), n-butane (UHP), and isobutane (UHP) were all purchased from Matheson.

Experimental Methods

The apparatus and procedure of the experiments have been described in Example 1, above. Any modifications are described below for this Example (see also "GC/FID Analytical Method" below). Briefly, a Parr reactor was used with a Teflon insert in the reactor along with a shaft and a thermowell coated with Teflon to prevent ozone decomposition on the metal surfaces.

A dioxygen stream was used to generate a mixture of ozone and dioxygen with the desired ozone mole fraction by an Atlas Ozone Generator, and it was charged into a reservoir equipped with a pressure transducer. Ar was then added into the reservoir to a desired pressure. Unless otherwise mentioned, the mixture contained about 5% $O_3$ and 45% $O_2$ with the balance being Ar. A Teflon-lined Parr vessel was evacuated at 80° C. under vacuum. The reactor was cooled and charged with the desired amounts of liquid alkanes (0.3 mol total alkanes) from an ISCO syringe pump cooled to 10° C. An option to direct the liquid alkane stream through a sample loop containing distilled water was provided to meter in controlled amounts of water. The reactor stirrer was set at 1000 rpm to allow the reactor to stabilize at the laboratory temperature around 24-25° C. Throughout a semi-batch run, the $O_2$+$O_3$+Ar mixture was supplied continuously to the reactor via a pressure regulator maintained at a constant pressure. The reaction conditions are provided in figure captions. The alkanes that escaped with the gas phase were partially condensed in a cold trap held around −60 to −50° C. and ambient pressure to concentrate the $CO_2$. The gas from the condenser was collected in Tedlar sample bags. At the end of a run, the reactor was placed in an ice bath kept in a freezer at −18° C. At this temperature, the vapor pressures of all compounds remaining in the reactor were very low (see "Saturation Vapor Pressures of Pure Components" below). Then a weighed amount of cold methanol was added into the reactor, and the reactor was kept around 0-4° C. to allow the remaining alkanes to vaporize and be condensed in the cold trap. The trap was maintained around −60 to −50° C. for butanes, and around −90° C. when propane was present. After adding 2-pentanone as an internal standard, the methanolic liquid sample was injected into an Agilent 7890A GC equipped with a flame ionization detector (FID) and a HP-PLOT/Q column to resolve≥$C_2$ products. The methanolic liquid sample was also added to $D_2O$ with maleic acid as an internal standard to quantify formic acid by $^1$H NMR spectroscopy. The gas samples collected in Tedlar bags were injected into another GC equipped with a thermal conductivity detector to analyze the $CO_2$, and an FID was used to analyze the hydrocarbons. More details of the GC/FID analytical methods are provided in "GC/FID Analytical Method" below.

The details of estimating alkane conversion (X), molar product selectivity, and $O_3$ utilization (U), as well as their confidence intervals, are provided in "Definitions of Conversion, Selectivity, and Ozone Utilization," below. The $O_3$ utilization was characterized by the ratio of utilized oxidizing equivalents from ozone/theoretical maximum oxidizing equivalents.

Results and Discussion

Ozonation of n-Butane

Although light alkane ozonation shares some common initiation mechanisms, n-butane as a sole substrate yielded a more complex product spectrum (n-$C_4$ in FIG. 1A) compared to isobutane as a sole substrate (i-$C_4$ in FIGS. 1A-1B). The major products from n-butane ozonation included 2-butanol, butanone, monocarboxylic acids, and $CO_2$. Sequential formation of 2-butanol, 2-butanone, and eventually carboxylic acids is possible. In separate experiments at ambient pressure and −20 to −10° C., it was confirmed that at the ozone/dioxygen fractions used in this Example, either a neat substrate (2-butanol or butanone) or a mixture of these substrates in $CCl_4$ can be oxidized; 2-butanol to butanone; and butanone to acids, 3-hydroxybutanone, and 2,3-butanedione. Given that high concentrations of both tert-butyl hydroperoxide and ozone mutually promote their decomposition possibly by forming excess free radicals, it was inferred that hydroperoxide may not form in significant amounts at the conditions used in this Example where high ozone utilization was observed. As for 3-hydroxybutanone and 2,3-butanedione as oxidation products from butanone, they formed in significant amounts only at relatively high concentrations of either 2-butanol or butanone.

Other possible routes for butanone formation include the direct elimination of a HOOH or a HOOOH from the respective polyoxide $(CH_3CH_2)(CH_3)HC—O_nH$ (n=2 or 3). Traces of proton signals from —OOH groups were observed in this Example. However, the origin of the hydroperoxide is unclear, since the ozonation of ketones and alcohols also produces hydroperoxide. Thus, the proton signals alone are insufficient to support the hydrogen peroxide elimination pathway. The observed overall stoichiometry of more than one mole oxygenate formation per mole ozone consumption could be related to oxidation by polyoxides (trioxide or peroxide). The high ozone utilization generally observed in this Example suggests that peroxide could not exist in high concentration. Further, peroxides cannot possibly activate butanols and butanes without a catalyst at ambient temperature. Therefore, trioxides are more likely involved; although at ambient temperature, they may be too unstable to observe by $^1$H NMR spectroscopy.

Due to the reactivity gap between n-butane and the products including 2-butanol and butanone, the foregoing over-oxidation is likely more competitive at consuming ozone compared to the alkane activation. Nonetheless, the biphasic gas-liquid process for n-butane ozonation resulted in low $CO_2$ formation (9%), especially compared to gas-phase ozonation (up to 78%), and has the added advantage of not employing any halogenated solvent (e.g., $CCl_4$). Because isobutane has been demonstrated to be more reactive than tert-butyl alcohol (TBA) during ozonation at similar conditions, the use of isobutane to suppress product over-oxidation was explored next.

Ozonation of Mixtures of n-Butane and Isobutane

In addition to evaluating the tunable selectivity in condensed phases, assessing the ozonation of butane mixtures may provide an alternate route for processing natural gas liquids without fractionation. While the $C_3$ and $C_4$ fractions in natural gas liquids exhibit a relatively wide volatility gap, such is not the case between n-butane and isobutane within the $C_4$ fraction ("Saturation Vapor Pressures of Pure Components," below). In other words, separation of the $C_4$ alkanes is more challenging and energy intensive by the distillation route. Hence, butane mixtures with different compositions were investigated with ozone at (25.0±0.6) ° C. to evaluate the effect of initial composition of the butane mixture on the observed products. Specifically, an isobutane to n-butane ratio (i/n) of 1.2 simulated the butane composition in a natural gas sample, while the other i/n ratios served as a sensitivity test due to the naturally varying compositions. The experiments were performed with either 100 μL (5.53 mmol) water addition or no initial water addition. It must be noted that water is a byproduct of the reactions forming C═O bonds. In the case of n-butane+isobutane mixtures, water formation as byproduct ranged from 0.1-0.2 mmol and 0.5-0.8 mmol without and with initial water addition, respectively. With only n-butane as feed, 0.5 and 2.2 mmol water formed without and with initially added water, respectively. Such amounts are smaller compared to the added water (5.53 mmol) found to be essential for effective ozone utilization.

The major products (defined as those having measured selectivity>0.1%) from neat isobutane ozonation included tert-butyl alcohol (TBA), acetone, formic acid, and $CO_2$, along with negligible formation of isobutyl alcohol, isobutyraldehyde, and tert-butyl hydroperoxide. As shown in FIGS. 1A-1B, n-butane alone as feed produced a complex oxygenate mixture including 2-butanol, butanone, butyric acid, propionic acid, acetic acid, and formic acid, accompanied by $CO_2$. Small quantities of a hydroperoxide (most likely 2-hydroperoxybutane) and acetone also formed. Despite the low yields, the peroxides could be a potential hazard during further processing if not decomposed.

The introduction of isobutane to the feed produced an unexpected significant effect on the product distribution. Along with butane conversions and ozone utilization, FIGS.

Figure 4:
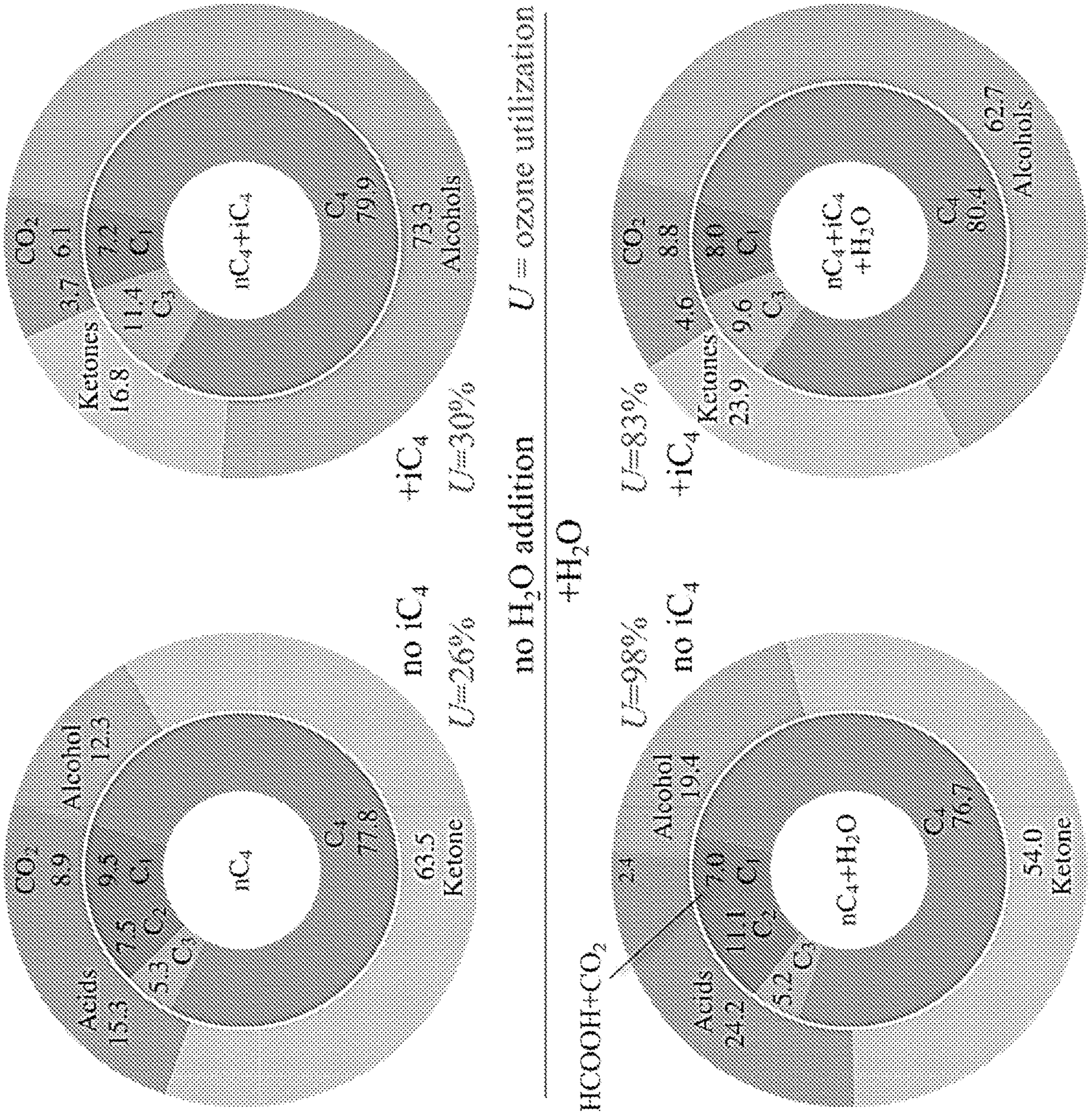
FIG. 4 provides an alternative way of illustrating the capability of the present processes in tuning product distribution by isobutane and water addition during the ozonation of various n-butane+isobutane mixtures (see also FIGS. 2A-2B). The reaction conditions were as follows: 25° C., 3.1±0.1 mmol $O_3$, 0.34 MPa $O_3$+$O_2$+Ar partial pressure, average residence time~6 min.

1A-1B show detailed product distributions, while FIG. 4 summarizes the effect of isobutane and water addition on n-butane conversion and product selectivity. The n-butane conversion and ozone utilization increased to three to four-fold with initial water addition (FIG. 1B) than without it (FIG. 1A). Either with or without water addition, both ozone utilization and ketones selectivity increased with increasing n-butane fraction in the feed. These results suggest that 2-butanol is highly reactive with ozone, with the oxidation to butanone consuming more ozone than the oxidation to 2-butanol. In contrast, tert-butyl alcohol was significantly more stable in the presence of ozone (ratio of overall oxidation rate for TBA/2-butanol≈$10^{-2}$), even at relatively high ozone content. In sharp contrast, ketone and acid formation from n-butane were less when isobutane was added to the feed up to an i/n=2 (FIG. 4), suggesting the C═O formation and C—C cleavage reactions are suppressed by the addition of isobutane. The progressive increase in isobutane content in the mixed $C_4$ feed tuned the product distribution (FIGS. 2A-2B). The butanone/2-butanol ratio decreased with isobutane addition (2.8 for neat n-butane and 1.9 for i/n=2.0), indicating that isobutane intercepted ozone to preferentially form TBA, thereby preventing further oxidation of the alcohol to ketone. This trend also suggests that 2-butanol oxidation is likely a significant route for butanone formation.

Mixtures of Isobutane and Propane

Motivated by the unexpected beneficial effect of isobutane in mixed butane feeds, mixtures of isobutane and propane were also evaluated. Unlike butane mixtures, the vapor pressures of propane+isobutane mixtures varied substantially in the range of the feed compositions studied, from 0.56 to 0.98 MPa. The reactor was pressurized with $O_3$+$O_2$+Ar mixtures such that both the $O_3$ and $O_2$ partial pressures were nearly invariant in all cases.

Figure 5:
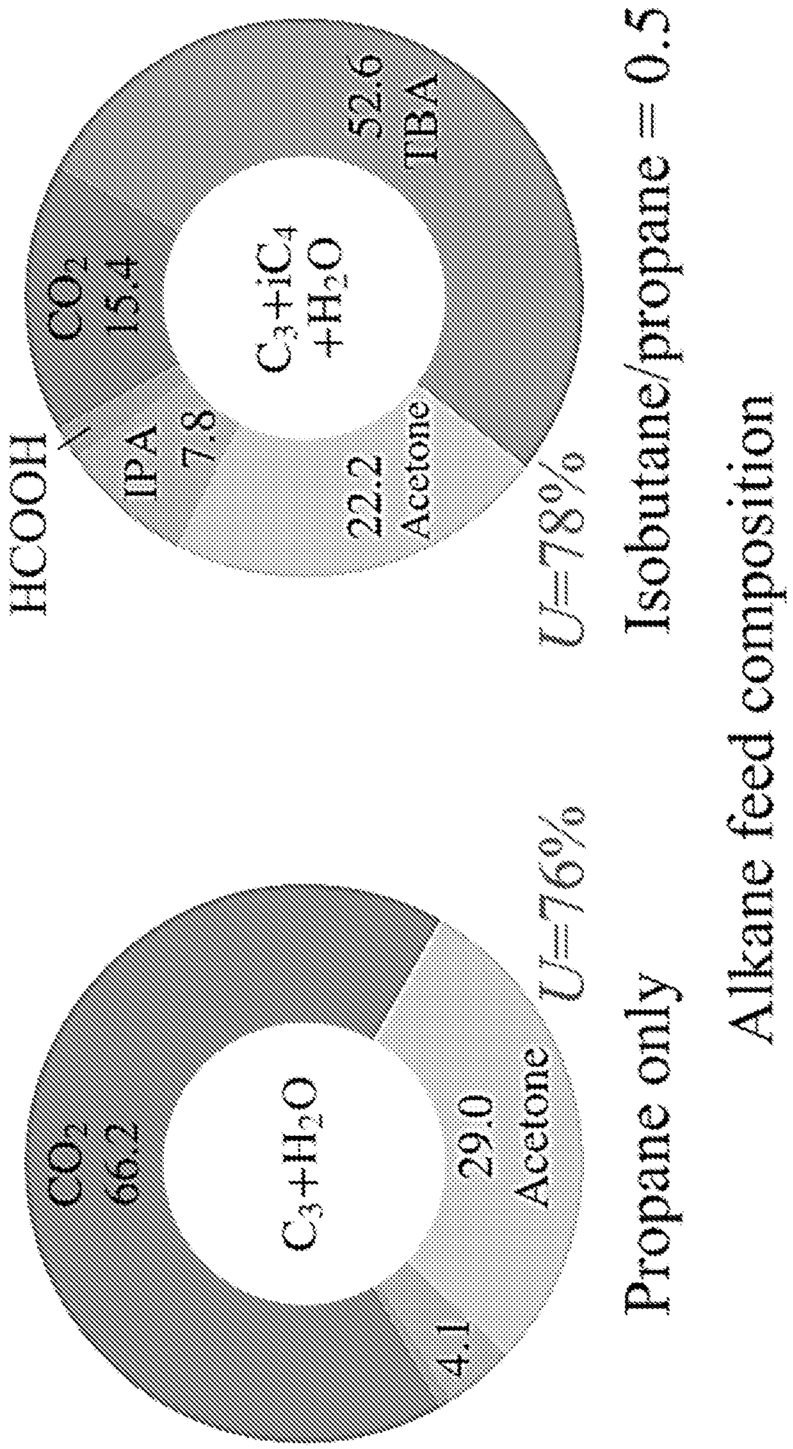
FIG. 5 provides an alternative way of illustrating the capability of the present processes in tuning product distribution and ozone utilization by isobutane and water addition during the ozonation of various propane+isobutane mixtures (see also FIG. 3). The reaction conditions were as follows: 24° C., 5.53 mmol water, 2.6±0.1 mmol $O_3$, 0.24 MPa $O_3$+$O_2$+Ar partial pressure, average residence time~15 min.
Figure 10:
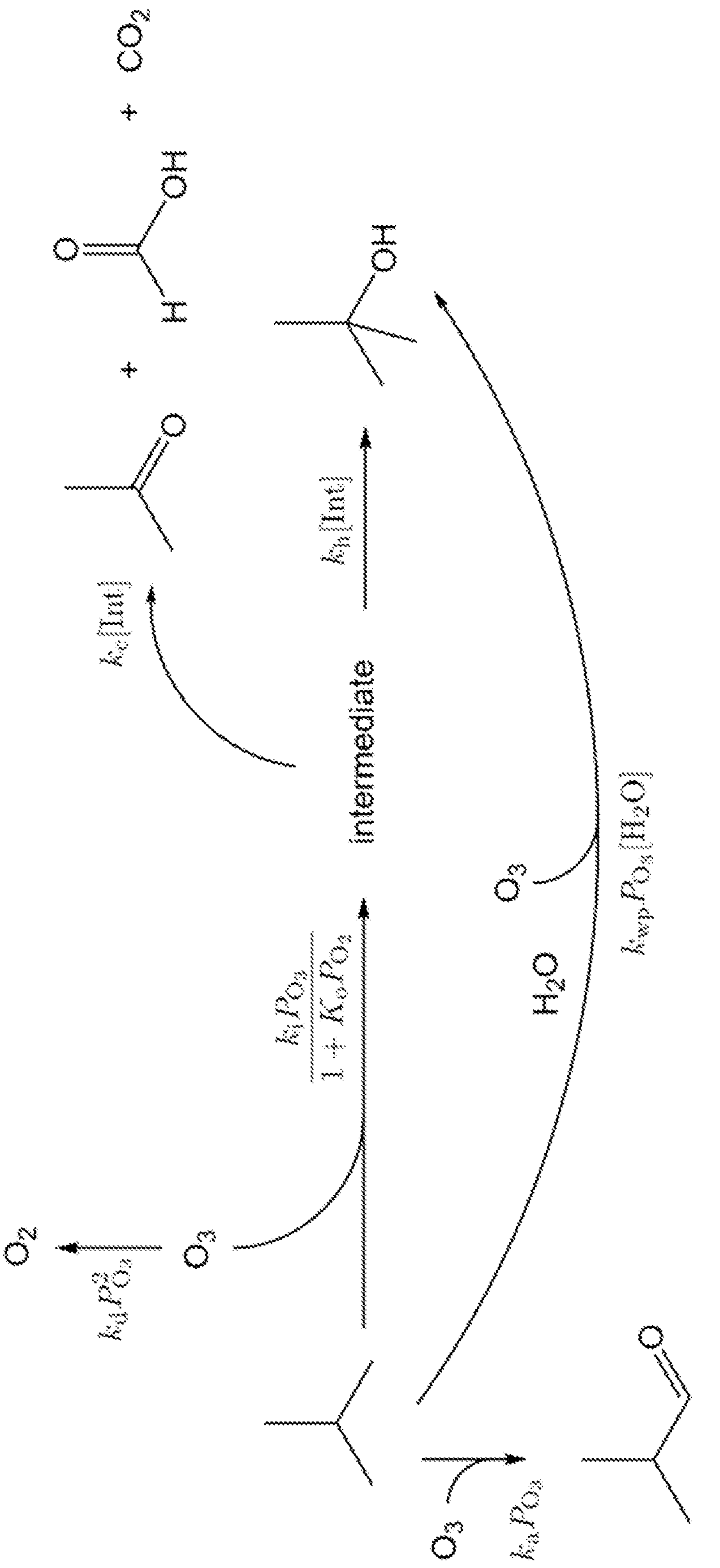
FIG. 10 shows possible reaction routes inferred from the mass balance equations.

Based on the products from n-butane ozonation, propane ozonation was expected to produce isopropyl alcohol (IPA), acetone, acetic acid, formic acid, and $CO_2$. However, acetic acid was not observed in any run (selectivity<<0.03%). Such observation suggests that the $C_3$ oxygenates are more prone to complete cleavage to $C_1$ products compared to the C—C cleavage of butanone. The absence of acetic acid also suggests that the enol-ozone route is probably less significant for acetone. As shown in FIG. 5, with only propane in the feed, the $CO_2$ selectivity was ~66%. The $C_3$ oxygenates are likely much more reactive with ozone compared to propane. As such, the effect of isobutane addition was even more pronounced for propane compared to n-butane. Adding 33 mole % isobutane doubled the IPA yield compared to neat propane and diminished the $CO_2$ selectivity drastically to ~16%, while increasing the overall hydrocarbon conversion. At 66 mole % isobutane in the feed, the $CO_2$ selectivity dropped even further to ~9% (see FIG. 3). Although the net oxidizing equivalents from ozone were similar in each case, ozone utilization was drastically shifted toward the desired oxygenate formation. The increased formation of IPA in the presence of isobutane at mild conditions is remarkable and suggests a potential low energy route for making propene from propane via IPA dehydration. Since acetone forms from both propane and isobutane ozonation, it is difficult to quantify the acetone produced from propane. However, an estimate could be made assuming that formic acid and $CO_2$ are (a) byproducts of acetone formation from isobutane and (b) products of complete C—C cleavage from propane ozonation (FIG. 10). For isobutane/propane ratios of 1-2, based on the ratios of (formic acid+$CO_2$)/acetone ("Definitions of Conversion, Selectivity, and Ozone Utilization," below), it was estimated that at most two thirds of the acetone formed from isobutane, i.e., at least one third of the acetone formed from propane.

Interestingly, only for neat propane, the product distribution from three runs varied more than the other cases. The large deviations in product selectivities between repeated runs along with the high $CO_2$ formation (see FIG. 3) suggests a free radicals-facilitated oxidation route that is potentially sensitive to impurities during propane ozonation. The isobutane addition to propane appears to inhibit such an unstable route by utilizing the ozone toward TBA formation, allowing much better control on the selectivity toward the desired products.

Ozonation of a Mixture of Butanes and Propane

Figure 6:
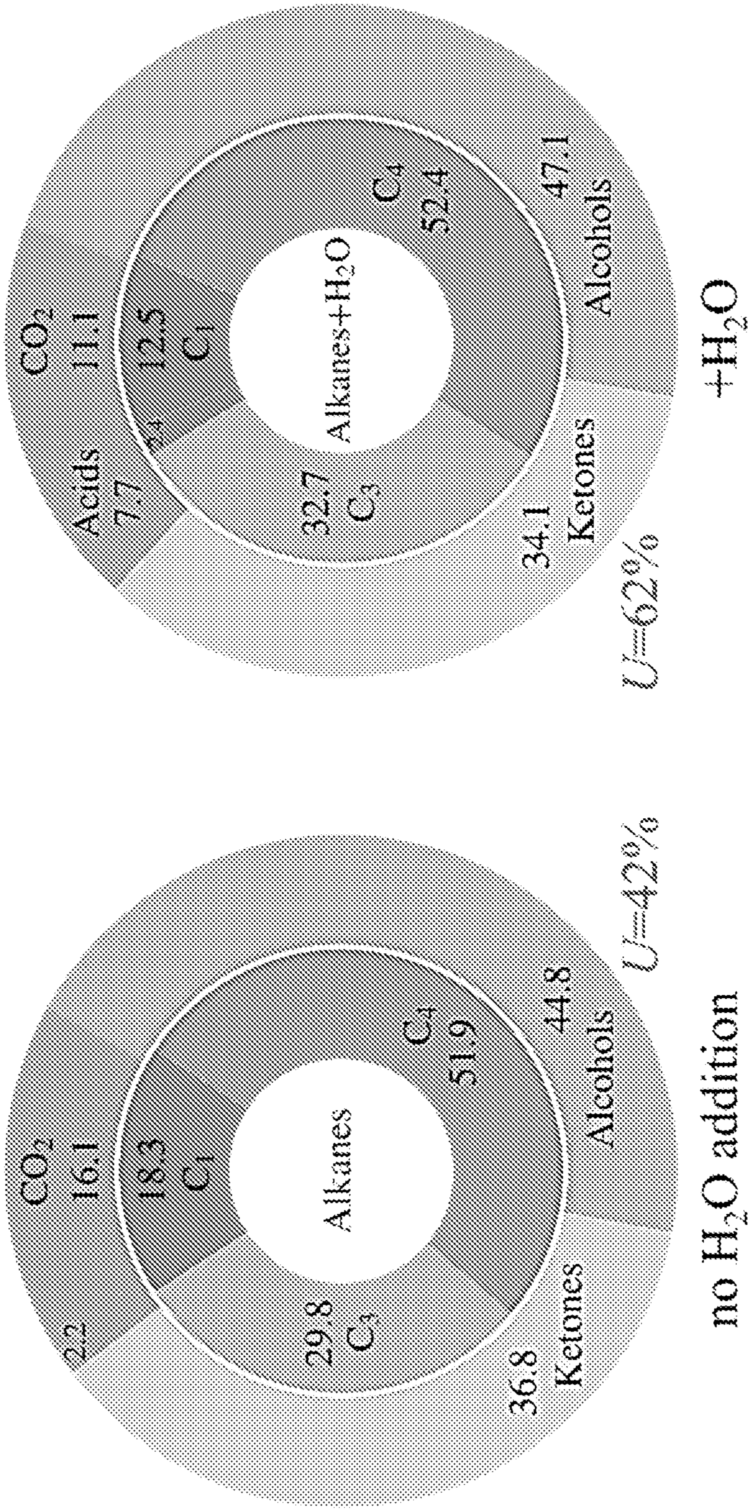
FIG. 6 illustrates the capability of the present processes in tuning product distribution and ozone utilization by the quantity of initially added water during the ozonation of a propane+n-butane+isobutane mixtures. The reaction conditions were as follows: Propane:n-butane:isobutane molar ratio=32:9:9 and 0.68 MPa, 24° C., 2.0±0.1 mmol $O_3$, 0.24 MPa $O_3$+$O_2$+Ar partial pressure, average residence time~15 min.
Figure 7:
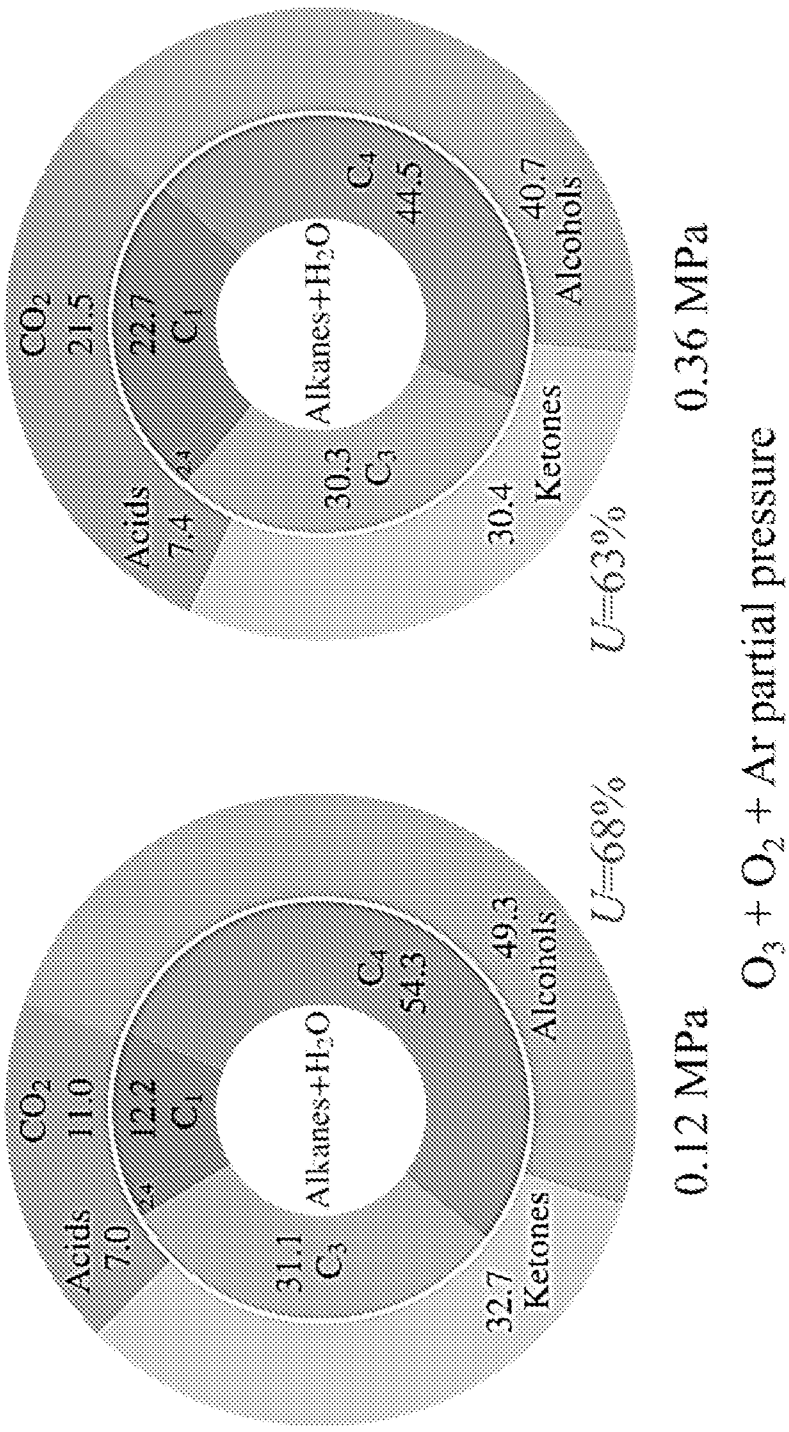
FIG. 7 illustrates the capability of the present processes in tuning product distribution and ozone utilization by the partial pressure of the $O_3$+$O_2$+Ar mixture during the ozonation of a propane+n-butane+isobutane mixtures. The reaction conditions were as follows: Propane:n-butane:isobutane molar ratio=32:9:9 and 0.68 MPa, 24° C., 5.53 mmol $H_2O$, 2.0±0.1 mmol $O_3$, average residence time~15 min.
Figure 8:
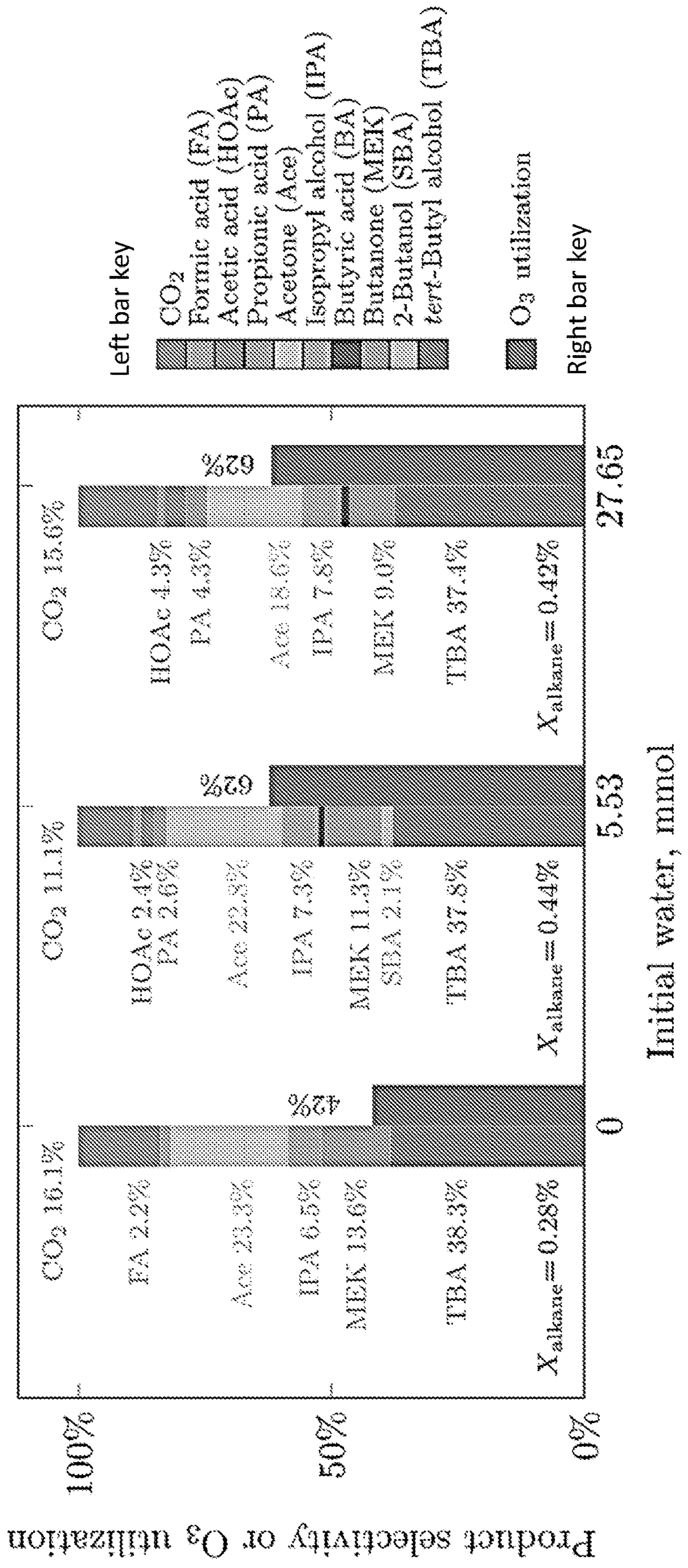
FIG. 8 provides an alternative way of illustrating the capability of the present processes in tuning product distribution and ozone utilization by the quantity of initially added water during the ozonation of a propane+n-butane+isobutane mixtures (see also FIG. 6). The reaction conditions were those used in FIG. 6.
Figure 9:
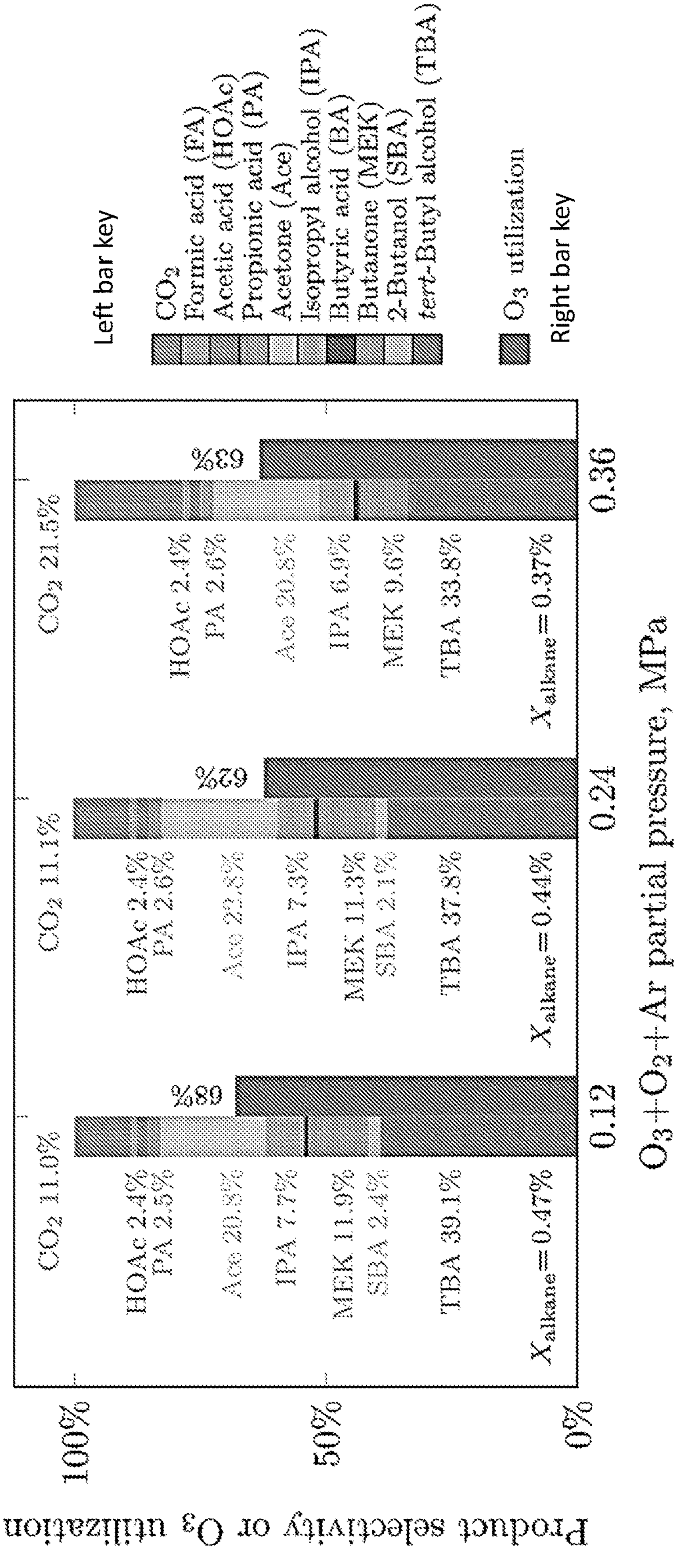
FIG. 9 illustrates the capability of the present processes in tuning product distribution and ozone utilization by the partial pressure of the $O_3$+$O_2$+Ar mixture during the ozonation of a propane+n-butane+isobutane mixtures (see also FIG. 7). Reaction conditions were those used in FIG. 7.

As discussed above, isobutane was shown to suppress over-oxidation when added to n-butane and propane, possibly by competing against the products (secondary alcohols and ketones) for ozonation. However, the actual $C_3$ and $C_4$ composition in natural gas liquids vary significantly due to the geological conditions. For example, the propane/isobutane ratio may be much higher (e.g., ~11). As such, a slower overall activation rate might occur during ozonation of $C_3$ and $C_4$ fractions, which could be detrimental to ozone utilization. By adding water and tuning ozone concentration in the liquid phase (by adjusting the partial pressure in the gas phase), improved ozone utilization was achieved as demonstrated by the results shown in FIGS. 6 and 7. The ternary feed used in these experiments simulates the propane, n-butane, and isobutane fractions found in typical natural gas samples. In sharp contrast to the progressive increase in ozone utilization when adding water (up to 27.7 mmol water) to the isobutane feed, the ozone utilization changed only marginally beyond 5.53 mmol water addition to the $C_3$+$C_4$ mixture (FIG. 8). Meanwhile, excess water promotes over-oxidation forming acids and $CO_2$. As shown in FIG. 9, a relatively low ozone partial pressure of 6 kPa (=5%×0.12 MPa) is most beneficial for minimizing ozone decomposition and product over-oxidation. As inferred from FIG. 9, the decrease in ozone utilization was milder at lower ozone partial pressures (between 12 and 18 kPa) compared to that observed during isobutane ozonation (between 17 and 24 kPa).

In contrast to isobutane ozonation where the relatively stable TBA is produced, greater product over-oxidation was observed in the case of mixed alkane feed. This was expected as the more reactive products, the secondary alcohols and ketones, may be oxidized more readily than the linear alkanes. In theory, this should have promoted ozone utilization. However, the opposite trend of ozone utilization with ozone partial pressure observed in FIG. 9 suggests that the ozone solubility may be different in propane and isobutane, resulting in differences in ozone decomposition kinetics. Various mechanisms of ozone decomposition may co-exist, characterized by either a first-order or a second-order decomposition kinetics in the gas phase. Such mixed reaction orders likely occur in the liquid phase as well. The relatively minor changes in product distribution and ozone utilization at low ozone partial pressures in FIG. 9 suggest that the apparent reaction orders for ozone decomposition and alkane activation are similar with respect to ozone (likely around first order). As ozone concentration increases, its decomposition may shift to higher apparent order in the liquid phase. This hypothesis was tested in the kinetic model discussed below, which confirms that ozone decomposition and alkane activation can indeed exhibit different reaction orders in liquid isobutane, thereby explaining the more varied effects of ozone partial pressure on ozone utilization.

Empirical Kinetic Modeling of Isobutane Ozonation

All ozonation experiments in this Example were carried out in a large excess of the alkane(s) in the liquid phase with good mixing that eliminated gas-liquid mass transfer limitations ("Estimating the Order of Magnitude for Ozone Mass Transfer Rate," below). The ozone and dioxygen concentrations in the liquid phase were dictated by their partial pressures in the gas phase. The substrate conversion in these experiments was very low (<2%), making the data ideal for kinetic modeling and analysis. However, the large number of ozonation products from mixed alkanes renders any modeling effort rather challenging. Given that isobutane forms fewer products and its presence has a major influence on product selectivities during the ozonation of mixed alkanes, the inventors decided to model the kinetics of neat isobutane ozonation. Experiments were designed to establish a relatively simple empirical model for isobutane ozonation that provided further clues about the possible reaction routes. The experimental details, the raw data, the various kinetic models tested, and the model regression procedure are detailed in "An Empirical Rate Model for Isobutane Ozonation," below. The rival kinetic models were assessed based on the relative quality of model predictions of the experimental data. Based on this procedure, the reaction network that best describes the experimental data on isobutane ozonation (see the parity plot of FIG. 11) is shown in FIG. 10. Table 1 shows values of the various kinetic parameters regressed from the experimentally observed product yields.

TABLE 1

Empirical kinetic parameters for isobutane ozonation.

| Constant | Value |
|---|---|
| $k_d$ | $(8.33 \pm 0.03) \times 10^{-1}$ mol · (L · min · bar$^2$)$^{-1}$ |
| $K_o$ | $(6.98 \pm 0.02) \times 10^{-1}$ bar$^{-1}$ |
| $k_i$ | $(3.56 \pm 0.02) \times 10^{-2}$ mol · (L · min · bar)$^{-1}$ |
| $k_c$ | $(1.20 \pm 0.02) \times 10^{-1}$ min$^{-1}$ |
| $k_h$ | $(1.00 \pm 0.02)$ min$^{-1}$ |
| $k_{wp}$ | $(3.87 \pm 0.09) \times 10^{-4}$ min$^{-1}$ · bar$^{-1}$ |
| $k_a$ | $(7.38 \pm 6.51) \times 10^{-5}$ mol · (L · min · bar)$^{-1}$ |
| $k_f$ | $(6.65 \pm 1.80) \times 10^{-2}$ |

At the low substrate conversions, the isobutane concentration was assumed to be invariant (≈the density of pure isobutane 9.47 mol/L) in the experiments and thus absorbed into the rate constants $k_i$, $k_a$, and $k_{wp}$. First order dependence of isobutane activation rate on ozone partial pressure ($P_{O3}$) was observed.

Compared to the estimated ranges of rate constants for propane and isobutane dehydrogenation on a variety of heterogeneous catalysts [~0.3 to 6 $mol_{alkane}$/(L·min), assuming a catalyst packing density~1 kg/L] at temperatures>450° C., the estimated rate constant for isobutane activation by ozone ($k_i$) was of a similar magnitude. This suggests that isobutane activation in its condensed phase by ozone is as facile at ambient temperature as its catalytic conversion by dehydrogenation at much higher temperatures.

The model additionally revealed a second order dependence of the ozone decomposition rate on $P_{O3}$. Compared to the typical rates of $O_3$ decomposition in the gas phase, the $O_3$ decomposition here occurred predominantly in the liquid phase. In addition, an apparent inhibition by dioxygen was revealed [as seen in the denominator of the $k_iP_{O3}/(1+K_oP_{O2})$ term], especially at low $P_{O3}$. The initiation steps of saturated hydrocarbons with ozone have been proposed to involve radical formation as follows.

R—H+$O_3$→R·+HOOO·→ROOOH→RO·+HOO·

RO·+R—H→ROH+R·

R·+$O_3$→ROOO·

The R· radical may be intercepted by dioxygen to produce a less active peroxyl intermediate slowing down the overall activation rate.

R·+$O_2$→ROO·

Thus, this inhibition effect could be evidence that the assumed intermediate shared by acetone and tert-butyl alcohol formation is likely to be tert-butyl hydrotrioxide or its derivative. Dioxygen potentially inhibits other reactions involving H-atom abstraction during the initiation steps, such as the ozonation of 2-butanol and n-butane.

Interestingly, the term expressing the water effect, $k_{wp}P_{O_3}$ [$H_2O$], describes a first order dependence each on the water concentration and the ozone partial pressure, but not on the concentration of the assumed intermediate shared by acetone and TBA formation (Eq. S4 below). Thus, water appears to promote a different route to form TBA from isobutane, most likely involving multiple elementary reactions. Ozone and water may also produce a pool of various species including $H_2O_x$ (neutral, x=2 or 3) and $HO_y$ (radical or anionic, y=1-5), which may interconvert and promote the activation of organic molecules. The water effect in this model may be a lumped representation of the formation of one or multiple intermediates from ozone and water, which then favor hydrogen abstraction from isobutane molecules.

The foregoing results of mixed alkane ozonation demonstrate that increasing isobutane content in the mixed alkane feed dictates product selectivity, by (a) tuning the ozone availability in the liquid phase, and (b) preferentially utilizing ozone to form active intermediates that not only promote the formation of tertiary butyl alcohol but also convert the linear alkanes in the feed to liquid oxygenates, while minimizing $CO_2$ formation. The product yields may be further optimized by fine-tuning the reaction conditions (isobutane content in feed, $O_2$ and $O_3$ partial pressures, and protic additives, in particular) to maximize ozone utilization and the yield of valuable liquid oxygenates.

Conclusions

Oxidation of mixed light alkanes by ozone to liquid oxygenates with high carbon atom economy (>90% combined selectivity to oxygenates and $CO_2$<10%) in their condensed phases at ambient temperature and mild pressures has been demonstrated herein. This is a significant improvement over the 55-78% $CO_2$ selectivities reported for the gas phase ozonation at 50° C. The results show an ability to control the ozone solubility, and therefore its availability, in the liquid phase by simply tuning the gas phase partial pressure. The significantly higher substrate concentrations in liquid phase compared to gas phase ozonation likely promote alkane activation even at ambient temperature. Thus, the biphasic nature of the reaction processes promotes effective utilization of ozone to create valuable alkane oxygenates rather than $CO_2$. Moreover, the addition of protic solvents to the liquid phase can direct preferred reaction pathways, which is challenging in a low-density gas phase. When water is added to the feed mixture, the ozone utilization increases with concurrent increases in alkane conversions and selectivity towards oxygenated products, with even less $CO_2$ formation. Finally, the unexpected beneficial effects of adding isobutane along with the water are especially pronounced with a mixed feed of propane and isobutane. These additives along with the facile tunability of ozone concentrations in light hydrocarbon liquid phases can be harnessed to maximize ozone utilization and C atom economy, promoting decarbonization and sustainability. This demonstration of facile and safe production of oxygenates, including alcohols, by a direct route from alkanes with high carbon atom economy and ozone utilization should elevate the promise of natural gas liquids as a viable feedstock for the chemical industry.

Additional Information for Example 2

Reaction and Analysis Procedure

While the product mixtures from propane and n-butane could be more complex than considered in Zhu, H. et al. *ACS Sustainable Chem. Eng.* 2021, 9 (16), 5506-5512, the experimental procedures for reactions, gas chromatography (GC) analysis with flame ionization detector (FID) or thermal conductivity detector (TCD), and $^1$H NMR analysis were adopted with some modifications. The changes and rationales are documented below and in the experimental section in Example 2, above.

Saturation Vapor Pressures of Pure Components

Saturation vapor pressures of liquid pure components at temperatures between −100° C. to 25° C. were considered. These include alkanes and common oxygenates in $C_1$-$C_4$ range, along with $CO_2$ and the internal standard for GC analysis, 2-pentanone. The components were grouped by their types (a—alkanes, b—aldehydes and ketones, c—alcohols, d—acids), except $CO_2$ (in a), hydroxyacetone (in b), and tert-butyl hydroperoxide (in d).

In a real mixture of products in either a liquid alkane or a polar solvent (methanol, acetonitrile, water, etc.), the vapor pressures of oxygenates were found to be generally lower than those of the respective pure compounds. Among these oxygenates, only formaldehyde and acetaldehyde may possibly have vapor pressures$\geq 10^5$ Pa at 25° C. and thus could possibly distribute significantly in the gas phase inside the reactor. However, a trap temperature between −70° C. and −60° C. is sufficiently low to condense most of these aldehydes as well as a large fraction of butanes within a relatively short residence time of the gas flow. These aldehydes were never detected by $^1$H NMR in the condensate from the reactor's gas effluent. They react with ozone rapidly even if any form.

When propane is present in the reactor, a trap around −90° C. can be used for condensing alkanes after reaction, but not during the semi-continuous run. As an example, a gas flow of approximately 1% $CO_2$ in 1:1 mol/mol propane-argon mixture retains about 30% of the $CO_2$ after being passed through a trap around −90° C.

Rationale for Using Teflon to Minimize the Effect of Transition Metal

Transition metals such as iron are known to affect product distribution during alkane ozonation. Further, transition metals can also facilitate the rapid decomposition of ozone. To avoid such potentially complex effects of transition metals, a Teflon insert in the reactor was used along with a shaft and a thermowell coated with Teflon to prevent the liquid phase from contacting metal parts of the Hastelloy reactor. In isobutane ozonation without the Teflon insert, ozone decomposition characterized by poor ozone utilization with larger deviations was observed.

Further, when evaluating the catalytic effect of Co, Ni, and Ti (~2 mg of the acetylacetonates of each metal in ~30 mL isobutane), various extents of ozone decomposition were observed. It is well known that transition metals and their oxides are employed to decompose ozone for treating tropospheric ozone pollution.

GC FID Analytical Method

The $^1$H NMR spectra collected from product mixtures in this Example were not well-resolved in 0-6 ppm range for product quantification, so their GC/FID chromatograms were used instead. The same Agilent HP-PLOT/Q megabore column used in Zhu, H. et al. *ACS Sustainable Chem. Eng.* 2021, 9 (16), 5506-5512 was used, but a different column oven program was developed in order to resolve oxygenates better. Upon injection, the oven was held at 40° C. for 5 min, ramped to 170° C. at 10° C./min, held at 170° C. for 10 min, ramped to 260° C. at 20° C./min, and finally held at 260° C. for 7.5 min. It was determined that most oxygenates$\geq C_2$ were separated using this oven program. Isobutyraldehyde and 1-propanol show dual peaks at retention times within 0.5 min, as shown by the obtained chromatogram of an oxygenate mixture. However, 1-propanol was never observed at the end of any run in this Example.

Other oven programs with even faster ramping stages may separate paraffin and olefin isomers$\leq C_4$ on a similar Agilent HP-PLOT/Q column. Thus, the GC methods in this Example should be adequate for detecting olefins if any form. However, olefins were never observed in any gas or liquid sample.

Definitions of Conversion, Selectivity, and Ozone Utilization

As butane oxidation is limited by the quantity of ozone, and the majority of the butanes are condensed during/after reaction (i.e., minor loss of the most volatile components), their conversions $X_{iC_4}$ and $X_{nC_4}$ were estimated from the total product yields from isobutane and n-butane ozonation as follows.

$$\frac{n_{iC_4,prod}}{n_{iC_4,0}} < X_{iC_4} < \frac{n_{iC_4,prod} + n_{C_1}/4}{n_{iC_4,0}},$$

$$\frac{n_{nC_4,prod}}{n_{nC_4,0}} < X_{nC_4} < \frac{n_{nC_4,prod} + n_{C_1}/4}{n_{nC_4,0}}.$$

Here $n_{iC_4,0}$ and $n_{nC_4,0}$ are the initial quantities of isobutane and n-butane, respectively. It is clear that tert-butyl alcohol and acetone form predominantly from isobutane, and that 2-butanol, butanone, butyric acid, propionic acid, and acetic acid form predominantly from n-butane. The total quantities of isobutane and n-butane converted to these products are $n_{iC_4,prod}$ and $n_{nC_4,prod}$, respectively.

$$n_{iC_4,prod} = n_{tert\text{-}butanol} + n_{acetone},$$

$$n_{nC_4,prod} = n_{sec\text{-}butanol} + n_{butanone} + n_{butyric\ acid} + n_{propionic\ acid} + n_{acetic\ acid}/2.$$

However, both isobutane and n-butane ozonation may form formic acid and $CO_2$, which are the $C_1$ minor products (total quantity is $n_{C_1}$). Thus, the upper and lower bounds for the conversions were estimated with the inequalities and then averaged to estimate the deviation shown in the figures.

$$n_{C_1} = n_{formic\ acid} + n_{CO_2}.$$

A scheme showing pathways for acetone, formic acid, and $CO_2$ formation from propane and isobutane is shown below.

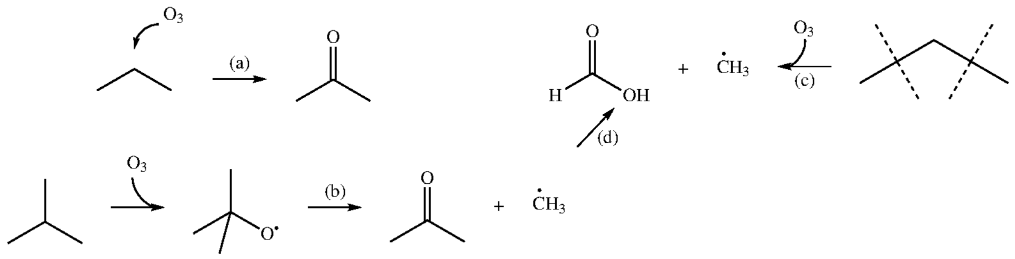

As shown in this scheme, during the ozonation of mixtures of isobutane and propane, acetone, formic acid, and $CO_2$ are the three common products from both alkanes. These products contribute to a significant fraction of the carbons in the products. Therefore, only the total conversion of alkanes $X_{C_xH_y}$ was estimated as follows.

$$\frac{n_{C_cH_y,prod}}{n_{C_xH_y,0}} < X_{C_xH_y} < \frac{n_{C_xH_y,prod} + n_{C_1}/3}{n_{C_xH_y,0}}.$$

Here, $n_{C_1}$ still denotes the total amounts of formic acid and $CO_2$. $n_{C_xH_y,0}$ is the total amount of alkanes initially charged into the reactor. $n_{C_xH_y,prod}$ is the estimated amount of converted alkanes based on the products, excluding $C_1$ products.

$$n_{C_xH_y,prod} = n_{tert\text{-}butanol} + n_{iso\text{-}butanol} + n_{isobutyraldehyde} + n_{iso\text{-}propanol} + n_{acetone}$$

Based on the stoichiometry of acetone/$CH_3\cdot$=1/1 in the scheme above and the following inequality, an upper bound for the fraction of acetone produced from isobutane may be estimated by the ratio of (formic acid+$CO_2$)/acetone.

$C_1$ products from isobutane≈Acetone from isobutane,

Total $C_1$ products>$C_1$ products from isobutane.

Therefore, $$\frac{\text{Acetone from isobutane}}{\text{Total acetone}} \approx \frac{C_1 \text{ from isobutane}}{\text{Total acetone}} < \frac{\text{Total } C_1 \text{ products}}{\text{Total acetone}}.$$

For neat propane, the propane conversion was estimated by $$X_{C_3H_8} = \frac{n_{iso\text{-}propanol} + n_{acetone} + n_{C_1}/3}{n_{C_3H_8,0}}.$$

The product selectivity for compound i is defined as follows, where the denominator is the total amount of all products that contain carbon atoms.

$$S_i = \frac{n_i}{\sum_j n_j}$$

The product distribution from a linear alkane is complex compared to only isobutane as feed when only three major products form. Therefore, a different definition for ozone utilization (U) was adopted as follows, in order to compare the total amount of oxidation achieved per mole of ozone. The net hydrocarbon oxidation was calculated on the basis of the changes in the formal carbon oxidation states in the oxygenated products relative to the hydrocarbon reactants. It should be noted that no reaction was observed with only dioxygen (i.e., without any ozone). However, in the presence of ozone, the dioxygen present in the mixture may be involved in the oxidation of radical intermediates at the conditions studied.

$$U = \frac{\text{net hydrocarbon oxidation}}{4 \times (\text{quantity of } O_3 \text{ introduced})} = \frac{n_e}{4n_{O_3}}$$

$$n_e = 2n_{tert\text{-}butanol} + 2n_{sec\text{-}butanol} + 4n_{butanone} + 3n_{acetone} + 6n_{butyric\ acid} + 5n_{propionic\ acid} + 5n_{acetic\ acid} + 5n_{formic\ acid} + 7n_{CO_2}$$

In all experiments, the cold trap and its contents were weighed directly to estimate the amount of condensed alkanes. The carbon balance is defined as follows. Per this definition, the C balance values in all experiments were in 94-99% range.

$$C = \frac{\text{amount of carbons in(condensed alkanes + products + gas samples)}}{\text{amount of carbons charged into reactor}}$$

$$\text{amount of carbons in products} = 4n_{tert\text{-}butanol} + 4n_{sec\text{-}butanol} + 4n_{butanone} + 3n_{acetone} + 4n_{butyric\ acid} + 3n_{propionic\ acid} + 2n_{acetic\ acid} + n_{formic\ acid} + n_{CO_2}$$

Detailed Product Distributions from Mixed Alkane Ozonation

These results are shown in FIGS. 2A-2B, 3, 8, and 9. The stacked bars were plotted in the same order as the legends in the figures. For the mixtures of n-butane and isobutane, FIGS. 2A and 2B group the product distribution shown in FIGS. 1A and 1B, by either the functional groups or the number of carbons in a molecule. For the mixtures of propane and isobutane, FIG. 3 shows the details of the results in FIG. 5. For the mixture of propane, n-butane, and isobutane, FIG. 8 (varying the quantity of initially added water) and FIG. 9 (varying the partial pressure of ozone) show the details of the results in FIG. 6 and FIG. 7, respectively.

An Empirical Rate Model for Isobutane Ozonation

To obtain better insights into the competition between ozone decomposition and isobutane activation, as well as the order of magnitude of the reaction rates, semi-continuous experiments were conducted to establish an empirical model for the reaction rates. The procedures were as described in the experimental section in Example 2, above, with relatively low ozone exposure (i.e., run time≤15 min). For some runs, the composition of the $O_3$+$O_2$+Ar gas mixture was varied.

The experimental data are listed in Table 2 showing the reaction conditions for each run. The rows above the middle bar (T through $P_{Ar}$) are the reaction conditions, while those below the bar (HCOOH through TBA) are the product amounts. In addition to the listed conditions, all experiments were carried out with stirring rates around 970-1020 rpm. Columns 1-5 were the first batch of planned experiments and carried out in randomized order. The data were regressed to provide information for planning the next batches. Columns 6-12 were the second batch, with some randomly selected repeats for the first batch. Further, to elucidate the effects of water content and dioxygen partial pressure, experiments in columns 13-18 were carried out.

$$\frac{d[Int]}{dt} = -k_c[Int] - k_h[Int] + \frac{k_i P_{O_3}}{1 + K_o P_{O_2}} \quad \text{Eq. S1b}$$

$$\frac{d[TBA]}{dt} = k_h[Int] + k_{wp} P_{O_3}[\mathrm{H_2O}] \quad \text{Eq. S1c}$$

$$\frac{d[\mathrm{Acetone}]}{dt} = k_c[Int] \quad \text{Eq. S1d}$$

TABLE 2

Product yields at various conditions used for the empirical model.

| | #1 | #2 | #3 | #4 | #5 | #6 | #7 | #8 | #9 |
|---|---|---|---|---|---|---|---|---|---|
| T, ° C. | 25.4 | 24.7 | 25.4 | 25.2 | 25.1 | 25.7 | 24.9 | 24.9 | 25.3 |
| Time, min | 5.58 | 5.76 | 10.22 | 5.84 | 14.81 | 6.52 | 10.35 | 5.88 | 14.74 |
| Initial $H_2O$, mmol | 5.53 | 27.64 | 5.53 | 5.53 | 27.64 | 5.53 | 5.53 | 16.59 | 5.53 |
| $O_3$, mmol | 0.88 | 0.88 | 1.56 | 0.89 | 2.26 | 0.99 | 1.67 | 0.95 | 2.38 |
| $O_2$, mmol | 7.54 | 7.86 | 13.94 | 7.99 | 20.14 | 8.92 | 15.06 | 8.56 | 21.46 |
| $P_{O3}$, bar | 0.178 | 0.174 | 0.175 | 0.175 | 0.174 | 0.173 | 0.174 | 0.174 | 0.176 |
| $P_{O2}$, bar | 1.54 | 1.56 | 1.56 | 1.57 | 1.56 | 1.55 | 1.57 | 1.57 | 1.59 |
| $P_{Ar}$, bar | 1.75 | 1.75 | 1.75 | 1.75 | 1.75 | 1.73 | 1.74 | 1.74 | 1.76 |
| HCOOH, mmol | 0.021 | 0.021 | 0.020 | 0.022 | 0.021 | 0.019 | 0.024 | 0.012 | 0.006 |
| $CO_2$, mmol | 0.11 | 0.12 | 0.22 | 0.11 | 0.32 | 0.15 | 0.20 | 0.11 | 0.31 |
| Acetone, mmol | 0.131 | 0.133 | 0.236 | 0.135 | 0.340 | 0.174 | 0.217 | 0.155 | 0.334 |
| iBuAl, mmol | 0.005 | 0.005 | 0.009 | 0.005 | 0.012 | 0.006 | 0.009 | 0.010 | 0.009 |
| TBA, mmol | 1.175 | 1.897 | 2.106 | 1.206 | 4.501 | 1.367 | 2.112 | 1.467 | 3.006 |

Note:
iBuAl = isobutyraldehyde, TBA = tert-butyl alcohol

TABLE 2

Product yields at various conditions used for the empirical model.

| | #10 | #11 | #12 | #13 | #14 | #15 | #16 | #17 | #18 |
|---|---|---|---|---|---|---|---|---|---|
| T, ° C. | 25.3 | 24.9 | 24.9 | 26.1 | 25.0 | 25.4 | 25.5 | 25.3 | 25.3 |
| Time, min | 10.20 | 10.19 | 5.70 | 5.91 | 12.50 | 10.30 | 9.67 | 9.50 | 9.46 |
| Initial H2O, mmol | 5.53 | 5.53 | 5.53 | 0 | 0 | 0 | 0 | 0 | 0 |
| $O_3$, mmol | 1.65 | 1.64 | 0.92 | 0.95 | 1.61 | 1.66 | 1.47 | 0.33 | 0.24 |
| $O_2$, mmol | 14.85 | 14.84 | 8.30 | 8.60 | 14.64 | 15.00 | 13.27 | 16.30 | 27.65 |
| $P_{O3}$, bar | 0.105 | 0.241 | 0.241 | 0.172 | 0.171 | 0.241 | 0.066 | 0.014 | 0.021 |
| $P_{O2}$, bar | 0.95 | 2.18 | 2.18 | 1.55 | 1.55 | 2.17 | 0.599 | 0.696 | 2.392 |
| $P_{Ar}$, bar | 1.05 | 2.42 | 2.42 | 1.72 | 1.73 | 2.41 | 0.665 | 0.710 | 1.034 |
| HCOOH, mmol | 0.004 | 0.005 | 0.013 | 0.012 | 0.009 | 0.004 | 0.029 | 0.006 | 0.005 |
| $CO_2$, mmol | 0.13 | 0.25 | 0.15 | 0.12 | 0.16 | 0.25 | 0.17 | 0.05 | 0.07 |
| Acetone, mmol | 0.282 | 0.292 | 0.226 | 0.156 | 0.239 | 0.277 | 0.205 | 0.054 | 0.047 |
| iBuAl, mmol | 0.007 | 0.010 | 0.009 | 0.009 | 0.011 | 0.009 | 0.007 | 0.006 | 0.006 |
| TBA, mmol | 2.002 | 2.196 | 1.267 | 1.004 | 2.213 | 1.863 | 1.574 | 0.687 | 0.442 |

Note:
iBuAl = isobutyraldehyde, TBA = tert-butyl alcohol

The following set of mass balance equations with reasonable simplicity were based on the scheme shown in FIG. 10 and were found to best represent the experimental data.

$$F_{O_3,in} - F_{O_3,out} = k_d P_{O_3}^2 + \frac{k_i P_{O_3}}{1 + K_o P_{O_2}} + k_{wp} P_{O_3}[\mathrm{H_2O}] + k_a p_{o_3} \quad \text{Eq. S1a}$$

$$\frac{d[\mathrm{Isobutyraldehyde}]}{dt} = k_a P_{O_3} \quad \text{Eq. S1e}$$

These are the mass balance of the reactor content including both the gas and the liquid phases, since oxygenates in the gas phase are condensed in the liquid phase when the reactor is equilibrated at −18° C. [i] ($mol/m^3$) represents the concentration of compound i. $F_{O_3,in}$ and $F_{O_3,out}$ ($mol \cdot m^{-3} \cdot s^{-1}$) represent the molar flow rates of ozone at the inlet and outlet, respectively. The average residence time of the gas flow was carefully chosen to achieve nearly total ozone conversion (i.e., $F_{O_3,out}\approx 0$). The concentration of an assumed intermediate is abbreviated as [Int]. While the first equation becomes a constraint only for the period with ozone supply, the differential equations are solved in two stages. The first has initial condition of zero product and intermediate amounts, and the second has initial concentrations immediately following the first stage but without ozone supply (i.e., $F_{O_3,in}=0$) to form any more intermediates (to simulate the reactions of the intermediates after the ozone cut-off).

The low yields of isobutyraldehyde and formic acid may not be reliably measured and modeled. Assuming the $C_1$ products were predominantly byproducts of acetone formation with such low ozone exposure, the formic acid quantity was estimated as $k_f\times$acetone quantity, and $CO_2$ as $(1-k_f)\times$ acetone quantity.

Figure 11:
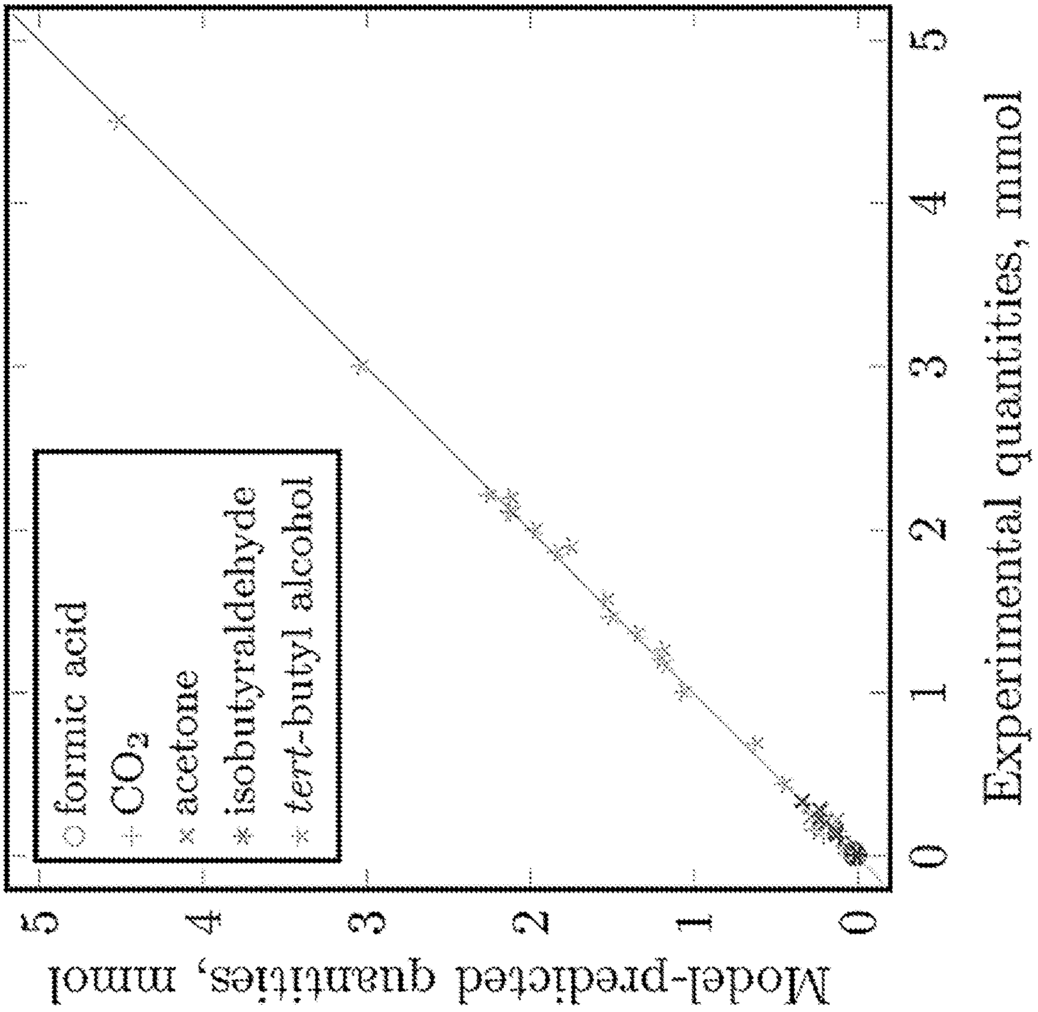
FIG. 11 shows a parity plot of model-predicted and experimental product amounts.

In addition, since the $CO_2$ in the gas samples was analyzed by the relatively less sensitive TCD, the absolute error for $CO_2$ measurement was greater than the error for all other products analyzed as liquid. To mitigate the disturbance from the errors of $CO_2$ quantification, the objective function to be minimized was partially scaled as follows.

$$F=\sum_j\sum_{i\neq CO_2}(n_{i,exp}-n_{i,pred})^2+S\sum_j\left(n_{CO_2,exp}-n_{CO_2pred}\right)^2$$

where index j is over all runs, and index i is over all compounds except $CO_2$. Subscript 'exp' denotes an experimental value, while 'pred' denotes a predicted value from the model by solving the equations as described above. S represents a scaling factor=the ratio of the average measurement error for other compounds divided by the error for $CO_2$. For these experiments, S=0.106≈0.003 mmol/0.030 mmol. The fitted parameters and their respective 95% confidence intervals are listed in Table 1. The parity plot in FIG. 11 compares the experimentally measured product quantities against the predictions by the empirical model with the values in Table 1.

Other Sets of Equations with Greater Deviations

As experimental data were obtained, regression was attempted with a few other sets of equations, which were revised to achieve the relatively small deviation shown above. To illustrate the necessity of some terms in the rate expressions related to TBA formation (i.e., to confirm the model is not overfitted), other sets resulting in greater deviations are appended below, as shown by the scattered points for TBA in the parity plots.

Compared to Eq. S1, the denominator term describing the inhibition by dioxygen, $1+K_oP_{O_2}$, is not included in Eq. S2. A resulting parity plot was obtained.

$$F_{O_3,in}-F_{O_3,out}=k_dP_{O_3}^2+k_iP_{O_3}+k_{wp}P_{O_3}[\mathrm{H_2O}]+k_aP_{O_3} \quad \text{Eq. S2a}$$

$$\frac{d[Int]}{dt}=-k_c[Int]-k_h[Int]+k_iP_{O_3} \quad \text{Eq. S2b}$$

$$\frac{d[TBA]}{dt}=k_h[Int]+k_{wp}P_{O_3}[\mathrm{H_2O}] \quad \text{Eq. S2c}$$

$$\frac{d[\text{Acetone}]}{dt}=k_c[Int] \quad \text{Eq. S2d}$$

$$\frac{d[\text{Isobutyraldehyde}]}{dt}=k_ap_{O_3} \quad \text{Eq. S2e}$$

Compared to Eq. S1, a first order decomposition rate with respect to ozone partial pressure is assumed in Eq. S3. A resulting parity plot was obtained.

$$F_{O_3,in}-F_{O_3,out}=k_dP_{O_3}+\frac{k_iP_{O_3}}{1+K_oP_{O_2}}+k_{wp}P_{O_3}[\mathrm{H_2O}]+k_aP_{O_3} \quad \text{Eq. S3a}$$

$$\frac{d[Int]}{dt}=-k_c[Int]-k_h[Int]+\frac{k_iP_{O_3}}{1+K_oP_{O_2}} \quad \text{Eq. S3b}$$

$$\frac{d[TBA]}{dt}=k_h[Int]+k_{wp}P_{O_3} \quad \text{Eq. S3c}$$

$$\frac{d[\text{Acetone}]}{dt}=k_c[Int] \quad \text{Eq. S3d}$$

$$\frac{d[\text{Isobutyaldehyde}]}{dt}=k_aP_{O_3} \quad \text{Eq. S3e}$$

Compared to Eq. S1, the TBA formation rate related to water is assumed to be first order with respect to the intermediate concentration in Eq. S4. A resulting parity plot was obtained.

$$F_{O_3,in}-F_{O_3,out}=k_dP_{O_3}^2+\frac{k_iP_{O_3}}{1+K_oP_{O_2}}+k_aP_{O_3} \quad \text{Eq. S4a}$$

$$\frac{d[Int]}{dt}=-k_c[Int]-k_h[Int]-k_{wp}[Int][\mathrm{H_2O}]+\frac{k_iP_{O_3}}{1+K_oP_{O_2}} \quad \text{Eq. S4b}$$

$$\frac{d[TBA]}{dt}=k_h[Int]+k_{wp}[Int][\mathrm{H_2O}] \quad \text{Eq. S4c}$$

$$\frac{d[\text{Acetone}]}{dt}=k_c[Int] \quad \text{Eq. S4d}$$

$$\frac{d[\text{Isobutyraldehyde}]}{dt} = k_a p_{O_3} \qquad \text{Eq. S4e}$$

Estimating the Order of Magnitude for Ozone Mass Transfer Rate

Since ozone is the limiting oxidant that initiates all reactions occurring during the ozonation of the alkanes (propane, n-butane, and isobutane), the comparison of the ozone consumption rate versus the gas-liquid mass transfer rate of ozone is essential to ensure that the observed yields are free of mass transfer limitation. Assuming closed mass balance, and that the ozone content in the reactor effluent is negligible, the overall ozone consumption rate was estimated to be $\leq 0.175$ mol/(L·min)$=9.72 \times 10^{-2}$ mol/(m$^3$·s). Using several dimensionless correlations for $k_L a$, the volumetric mass transfer coefficient, empirically predicted values of the gas-liquid mass transfer rate of ozone were calculated to estimate a lower bound. The $k_L a$ values listed in Table 3, below, were estimated with the physical and transport properties below.

The diffusivity values of ozone in liquid alkanes were estimated with the empirical correlation implemented in Aspen Plus: $D_L \geq 3.20 \times 10^{-8}$ m$^2$/s, which is fairly close to ozone diffusivity in water. The density of the liquid was assumed to be between the densities of pure propane and pure isobutane: 476 kg/m$^3 < \rho < 550$ kg/m$^3$. The stirring rate was about 1000 rpm: N$=(16.59 \pm 0.51)$ s$^{-1}$. The liquid viscosity was assumed to be less than that of pure n-butane: $\mu < 1.59 \times 10^{-4}$ Pa·s. The superficial gas velocity was estimated from the gas flow rate through the cross-section of the reactor: $v_s > 8.1 \times 10^{-4}$ m/s. The surface tension was assumed to be less than that of pure n-butane: $\sigma < 1.19 \times 10^{-2}$ N/m. The viscosity values for the gas mixture were estimated with Eq. S5: $\mu_G \geq 1.36 \times 10^{-5}$ Pa·s. Gravitational constant g$=9.81$ m/s$^2$.

$$\mu_G = \frac{\sum_i y_i \mu_i \sqrt{M_i}}{\sum_i y_i \sqrt{M_i}} \qquad \text{Eq. S5}$$

where $y_i$, $\mu_i$, and $M_i$ are the mole fraction, the viscosity, and the molecular weight of component i, respectively

TABLE 3

Estimated volumetric mass transfer coefficients for continuously stirred systems.

| Dimensionless correlation[4] | Lower bound for $k_L a$, s$^{-1}$ |
|---|---|
| $\dfrac{k_L a T^2}{D_L} = 21.2 \left(\dfrac{\rho N T}{\mu}\right)^{1.11} \left(\dfrac{\mu}{\rho D_L}\right)^{0.5} \left(\dfrac{v_s T}{\sigma}\right)^{0.45} \left(\dfrac{\mu_G}{\mu}\right)^{0.69}$ | 14.1 |
| $\dfrac{k_L a T^2}{D_L} =$ | 0.54 |
| $0.06 \left(\dfrac{\mu}{\rho D_L}\right)^{0.5} \left(\dfrac{T^2 N \rho}{\mu}\right)^{1.5} \left(\dfrac{\mu v_s}{\sigma}\right)^{0.6} \left(\dfrac{N^2 T}{g}\right)^{0.19} \left(\dfrac{N T}{v_s}\right)^{0.32}$ | |
| $\dfrac{k_L a T^2}{D_L} = 8.38 \left(\dfrac{\rho N T^2}{\mu}\right)^{2/3} \left(\dfrac{\mu}{\rho D_L}\right)^{1/3}$ | 0.83 |
| $\left(\dfrac{\rho N^2 T^2}{\sigma}\right)^{0.43} \left[1 + 1.5 \times 10^{-3} \left(\dfrac{\rho N^2 T^3}{\sigma}\right)\right] \left(\dfrac{N T}{v_s}\right)^{-0.4} \left(\dfrac{T}{D}\right)$ | |

TABLE 3-continued

Estimated volumetric mass transfer coefficients for continuously stirred systems.

| Dimensionless correlation[4] | Lower bound for $k_L a$, s$^{-1}$ |
|---|---|
| $\dfrac{k_L a T^2}{D_L} = 1.41 \times 10^{-3} \left(\dfrac{\mu}{\rho D_L}\right)^{0.5} \left(\dfrac{T^2 N \rho}{\mu}\right)^{0.67} \left(\dfrac{\rho N^2 T^3}{\sigma}\right)^{1.29}$ | 0.16 |

Due to the fast reaction rate of ozone in the liquid phase, the ozone concentration in the bulk liquid phase, $C_{O_3}$, should be negligible compared to the saturation ozone concentration in the liquid alkane, $C_{O_3}^*$. Table 4, below, lists the Henry's law constants estimated with Eq. S6a-c from the reported dimensionless solubility $\alpha$ of O$_3$ in CCl$_4$. Based on these values, the $C_{O_3}^*$ in liquid isobutane should be at least on the order of $10^1$ mol/m$^3$ at the reaction conditions. Thus, even based on the lowest estimate for $k_L a$, the minimum gas-liquid mass transfer rate $(k_L a)(C_{O_3}^* - C_{O_3}) = 1.6$ mol/(m$^3$·s). The value is more than one order of magnitude greater than the actual ozone consumption rate $9.72 \times 10^{-2}$ mol/(m$^3$·s), thus confirming that the observed reaction rates are not limited by the gas-liquid mass transfer of ozone.

$$\alpha = \frac{c_{O_3,L}}{c_{O_3,G}} \qquad \text{Eq. S6a}$$

$$P_{O_3,G} = c_{O_3,G} RT \qquad \text{Eq. S6b}$$

$$k_H = \frac{c_{O_3,L}}{P_{O_3,G}} = \frac{\alpha}{RT} \qquad \text{Eq. S6c}$$

where $c_{O_3,L}$ and $c_{O_3,G}$ are the ozone concentrations in the liquid and gas phases, respectively. $P_{O_3,G}$ is the ozone partial pressure in the gas phase.

TABLE 4

Ozone solubility in tetrachlorocarbon at 263 to 298K.

| T, K | $\alpha$ | $k_H$, mol · (L · bar)$^{-1}$ |
|---|---|---|
| 263 | 5.1 | 0.23 |
| 273 | 4.4 | 0.19 |
| 293 | 2.9 | 0.12 |
| 298 | 2.6 | 0.10 |

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

If not already included, all numeric values of parameters in the present disclosure are proceeded by the term "about" which means approximately. This encompasses those variations inherent to the measurement of the relevant parameter as understood by those of ordinary skill in the art. This also encompasses the exact value of the disclosed numeric value and values that round to the disclosed numeric value.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A process for oxidizing an alkyl substrate, the process comprising combining an alkyl substrate and ozone in a liquid phase medium comprising a branched alkane activator and a protic additive, wherein the branched alkane activator is a compound capable of reacting with the ozone to form a hydrotrioxide intermediate and the protic additive is a compound capable of forming a hydrogen bond with the hydrotrioxide intermediate, and further wherein the ozone oxidizes the alkyl substrate to products comprising an alcohol, wherein the alkyl substrate is selected from linear and cyclic alkanes.

2. The process of claim 1, wherein the alkyl substrate is selected from linear alkanes.

3. The process of claim 2, wherein the linear alkanes comprise propane, n-butane, or both.

4. The process of claim 1, wherein the branched alkane activator comprises a tertiary carbon.

5. The process of claim 1, wherein the branched alkane activator is an isoalkane.

6. The process of claim 1, wherein the branched alkane activator has from 4 to 8 carbons.

7. The process of claim 1, wherein the branched alkane activator is isobutane.

8. The process of claim 1, wherein the branched alkane activator is present in the liquid phase medium at an activator-to-alkyl substrate mole ratio of greater than 0.2 and the protic additive is present in the liquid phase medium at an amount of at least 0.1 mol %.

9. The process of claim 1, wherein the branched alkane activator is isobutane and the alkyl substrate comprises propane, n-butane, or both.

10. The process of claim 1, further comprising adding the protic additive to the liquid phase medium prior to oxidizing the alkyl substrate.

11. The process of claim 1, wherein the protic additive is water, an alcohol having from 1 to 6 carbons, or a combination thereof.

12. The process of claim 1, wherein the liquid phase medium comprises no more than 0.4 mol % $CO_2$.

13. The process of claim 1, wherein the liquid phase medium is free of added $CO_2$.

14. The process of claim 8, wherein the combining is carried out at a temperature of at least 15° C. and a total pressure of a vapor phase present above the liquid phase medium of no more than 5 MPa.

15. The process of claim 1, wherein the products comprise the alcohol at a selectivity of at least 50%, the products comprise $CO_2$ at a selectivity of no more than 10%, the process has an ozone utilization value of at least 75%, or a combination thereof.

16. The process of claim 1, wherein the products comprise the alcohol at a selectivity of at least 50%, the products comprise $CO_2$ at a selectivity of no more than 10%, and the process has an ozone utilization value of at least 75%.

17. The process of claim 1, wherein the alkyl substrate is a linear alkane, and further wherein the liquid phase medium is free of added $CO_2$, and the process further comprises adding the protic additive to the liquid phase medium prior to oxidizing the linear alkane.

18. The process of claim 1, wherein the branched alkane activator comprises a tertiary carbon; and the protic additive is water, an alcohol having from 1 to 6 carbons, or a combination thereof.

19. The process of claim 18, wherein the branched alkane activator is present in the liquid phase medium at an activator-to-alkyl substrate mole ratio of greater than 0.2 and the protic additive is present in the liquid phase medium at an amount of at least 0.1 mol % and wherein the combining is carried out at a temperature of at least 15° C. and a total pressure of a vapor phase present above the liquid phase medium of no more than 5 MPa.

20. The process of claim 19, wherein the branched alkane activator has from 4 to 8 carbons and the alcohol is selected from methanol, ethanol, isopropanol, tert-butyl alcohol, and combinations thereof.

* * * * *